United States Patent
Martinelli et al.

(10) Patent No.: US 11,434,225 B2
(45) Date of Patent: Sep. 6, 2022

(54) SALTS AND SOLID STATE FORMS OF PLINABULIN

(71) Applicant: PLIVA HRVATSKA D.O.O., Zagreb (HR)

(72) Inventors: Marisa Martinelli, Villa Guardia (IT); Pavel Kolesa, Haj Ve Slezsku (CZ); Donato Motolese, Brugherio (IT); Paolo Simone Tiseni, Bresso (IT)

(73) Assignee: PLIVA HRVATSKA D.O.O., Zagreb (HR)

( * ) Notice: Subject to any disclaimer, the term of this patent is extended or adjusted under 35 U.S.C. 154(b) by 16 days.

(21) Appl. No.: 16/635,656

(22) PCT Filed: Aug. 1, 2018

(86) PCT No.: PCT/US2018/044815
§ 371 (c)(1),
(2) Date: Jan. 31, 2020

(87) PCT Pub. No.: WO2019/028144
PCT Pub. Date: Feb. 7, 2019

(65) Prior Publication Data
US 2021/0122738 A1 Apr. 29, 2021

Related U.S. Application Data

(60) Provisional application No. 62/586,239, filed on Nov. 15, 2017, provisional application No. 62/563,825, (Continued)

(51) Int. Cl.
*C07D 403/06* (2006.01)

(52) U.S. Cl.
CPC ........ *C07D 403/06* (2013.01); *C07B 2200/13* (2013.01)

(58) Field of Classification Search
None
See application file for complete search history.

(56) References Cited

U.S. PATENT DOCUMENTS 7,064,201 B2  6/2006 Hayashi et al.

FOREIGN PATENT DOCUMENTS

| WO | 2017011399 A1 | 1/2017 |
| WO | 2018028420 A1 | 2/2018 |

OTHER PUBLICATIONS

Mino R. Caira, "Crystalline Polymorphism of Organic Compounds", Topics in Current Chemistry; Springer, Berline, DE, vol. 198, pp. 163-208 (1998).

(Continued)

*Primary Examiner* — Clinton A Brooks
(74) *Attorney, Agent, or Firm* — Carter, DeLuca & Farrell LLP

(57) ABSTRACT

The present disclosure relates to Plinabulin solid state forms, Plinabulin salts including hydrochloride and solid state forms thereof, processes for preparation thereof and pharmaceutical compositions thereof.

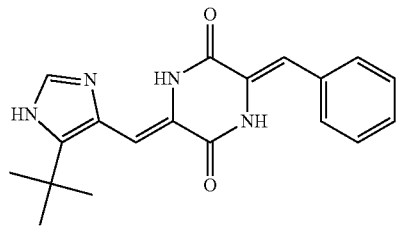

12 Claims, 16 Drawing Sheets

Related U.S. Application Data filed on Sep. 27, 2017, provisional application No. 62/540,653, filed on Aug. 3, 2017.

(56) References Cited

OTHER PUBLICATIONS

International Search Report and Written Opinion of the International Searching Authority issued in corresponding Int'l Appl. PCT/US2018/044815 dated Nov. 22, 2018 (20 pages).

Figure 1: XRPD pattern of Plinabulin Form A obtained in Example 1
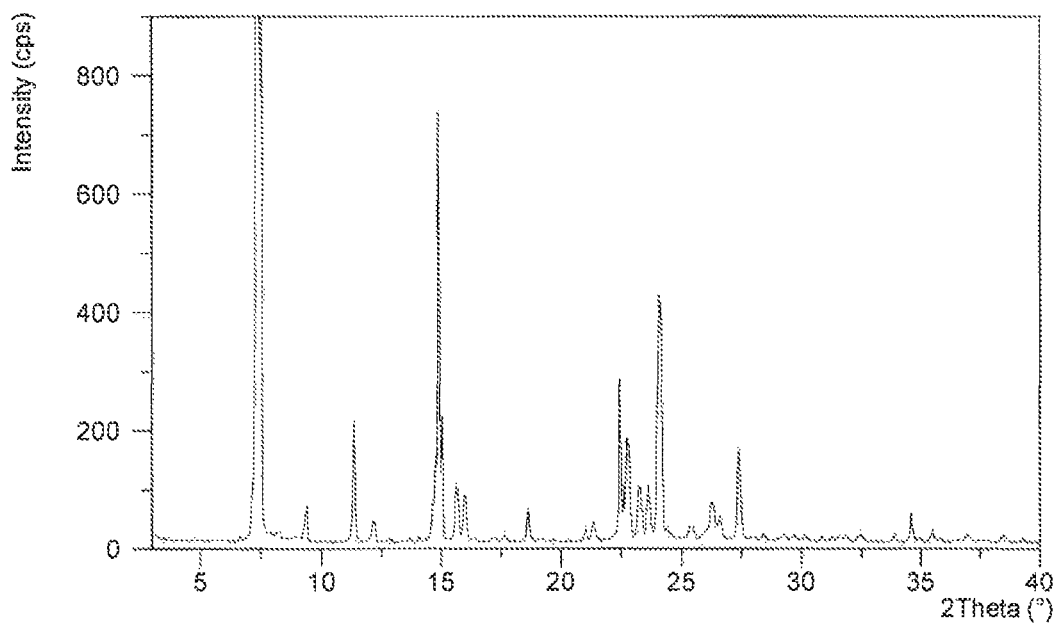
Figure 2: XRPD pattern of Plinabulin Form B obtained in Example 2
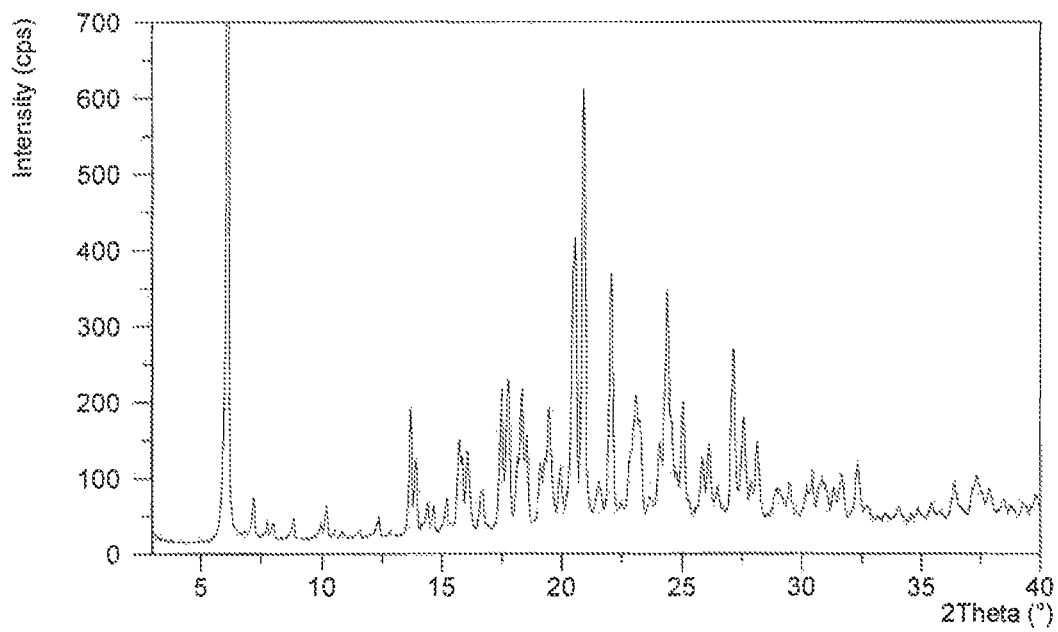

Figure 3: XRPD pattern of Plinabulin Form C obtained in Example 3
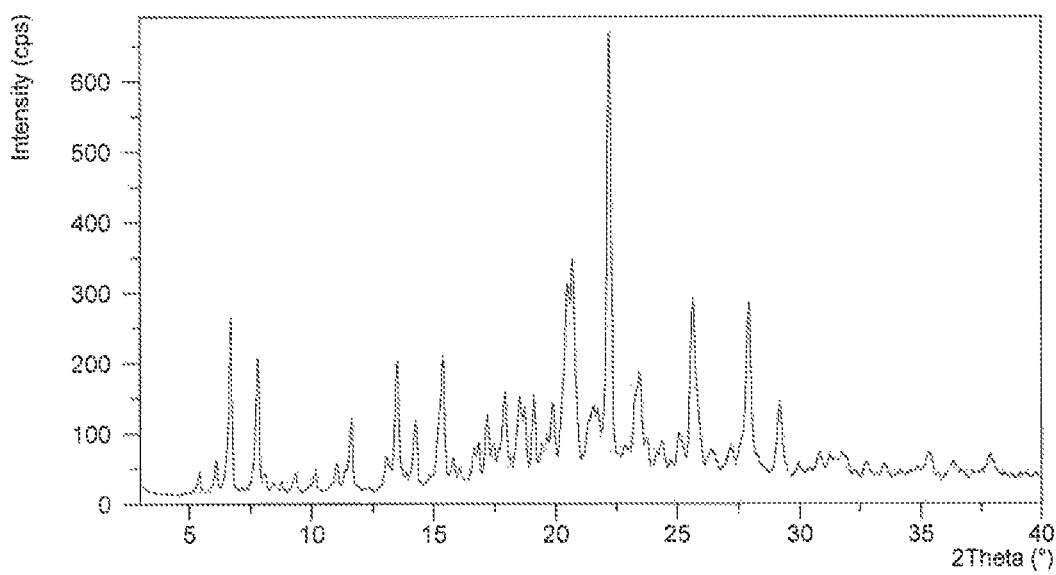
Figure 4: XRPD pattern of Plinabulin Form D obtained in Example 4
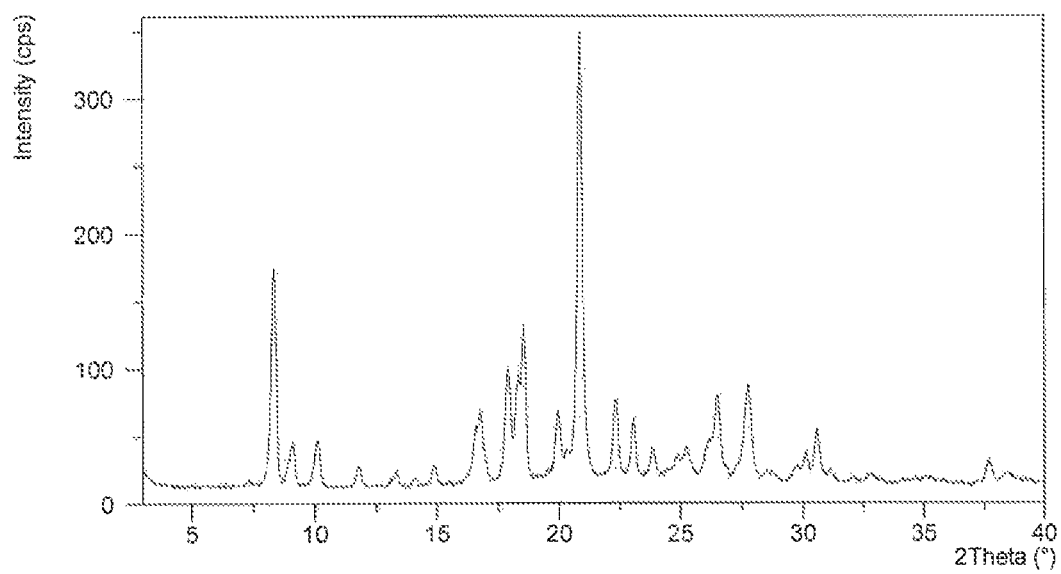

Figure 5: XRPD pattern of Plinabulin Form E obtained in Example 5
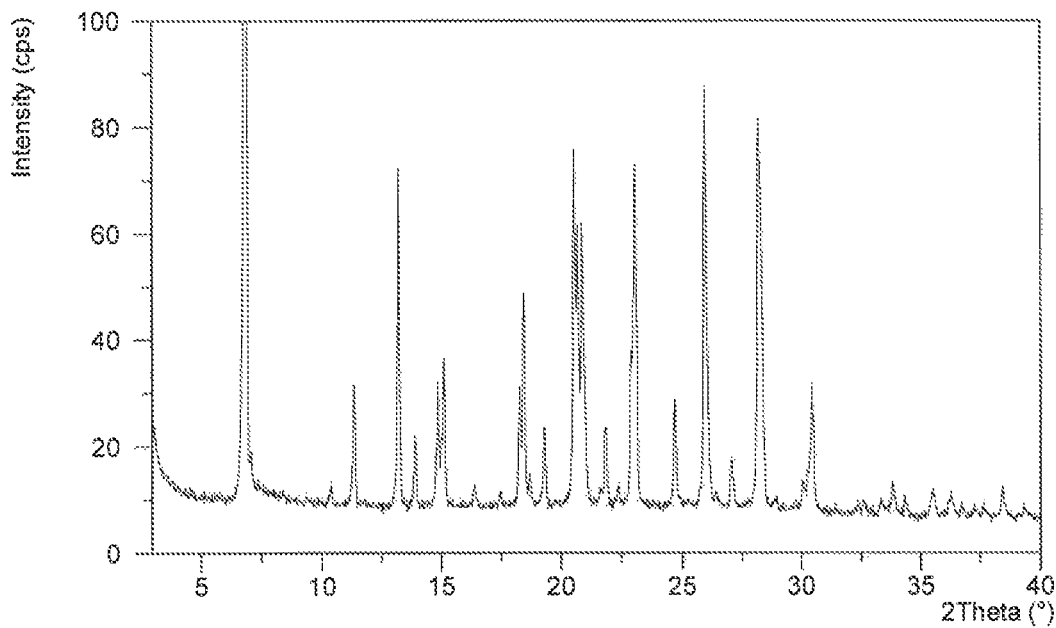
Figure 6: XRPD pattern of Plinabulin Form F obtained in Example 6
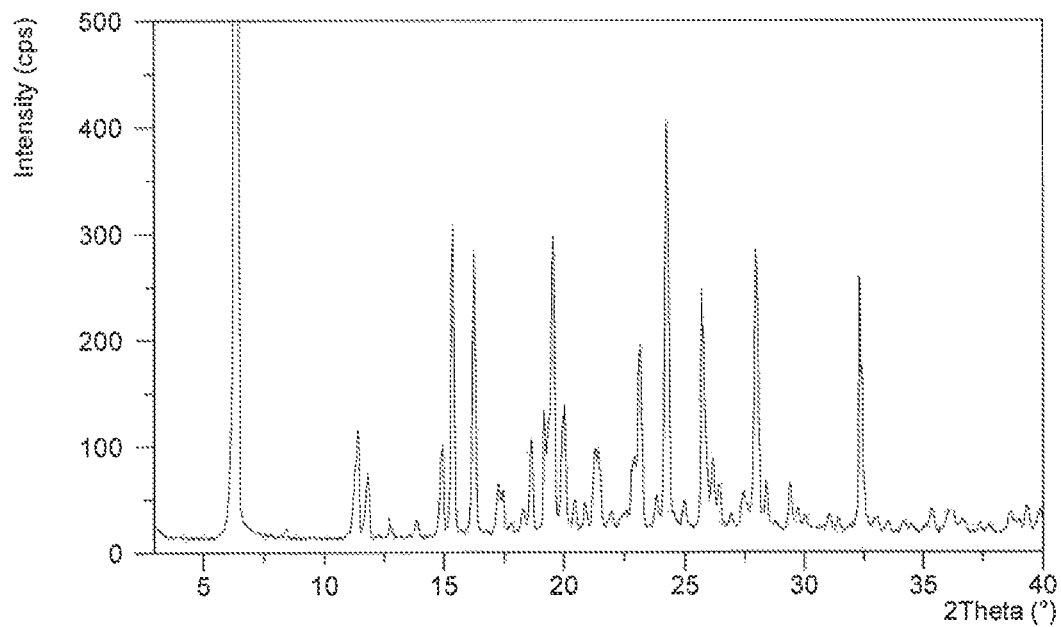

Figure 7: XRPD pattern of Plinabulin Form G obtained in Example 7
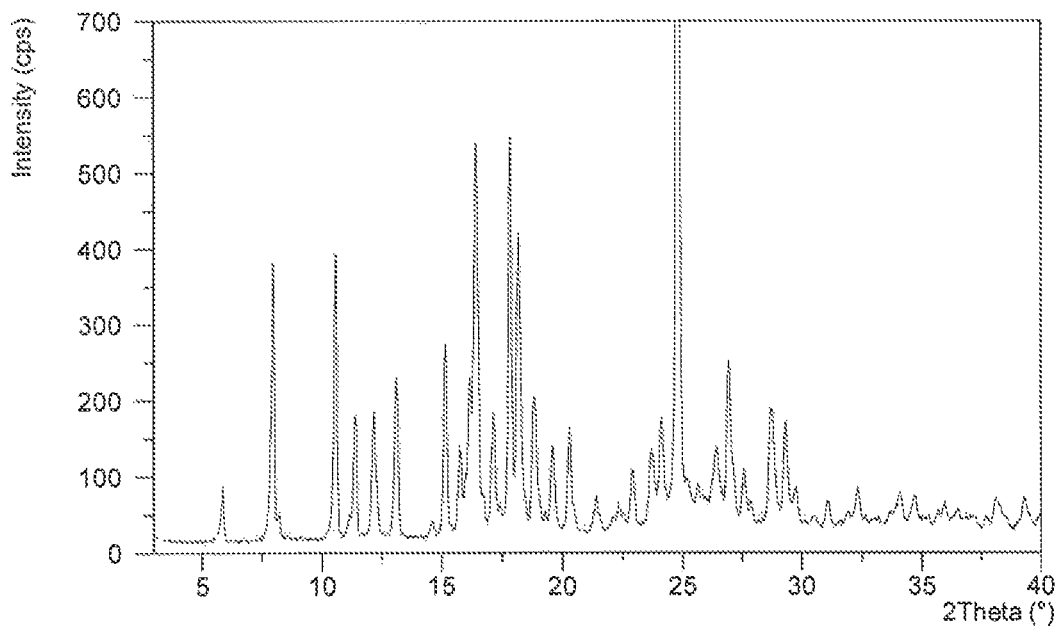
Figure 8: XRPD pattern of Plinabulin hydrochloride salt Form Alpha obtained in Example 8
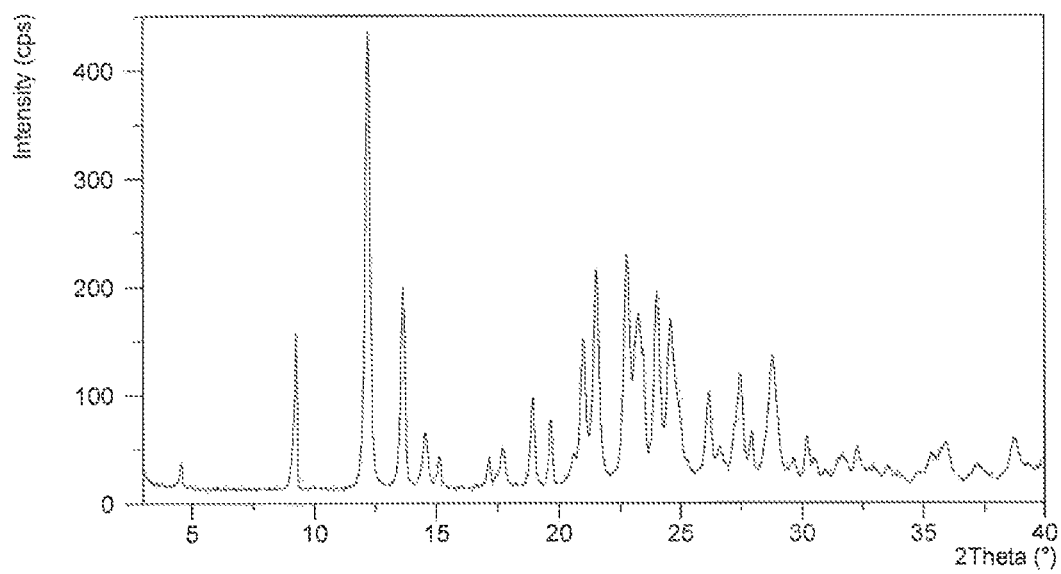

Figure 9: XRPD pattern of form 1 which is described in PCT application WO2017011399.
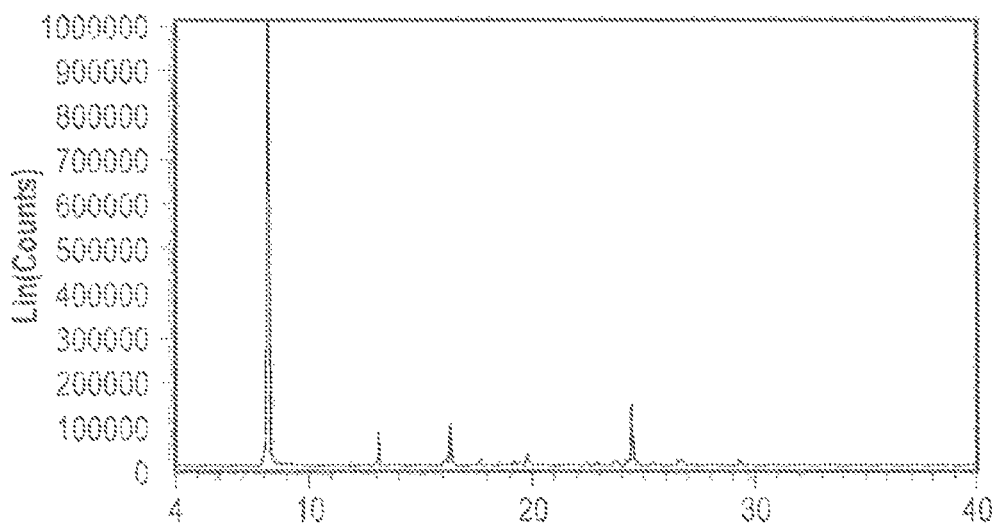
Figure 10: XRPD pattern of form 5 which is described in PCT application WO2017011399.
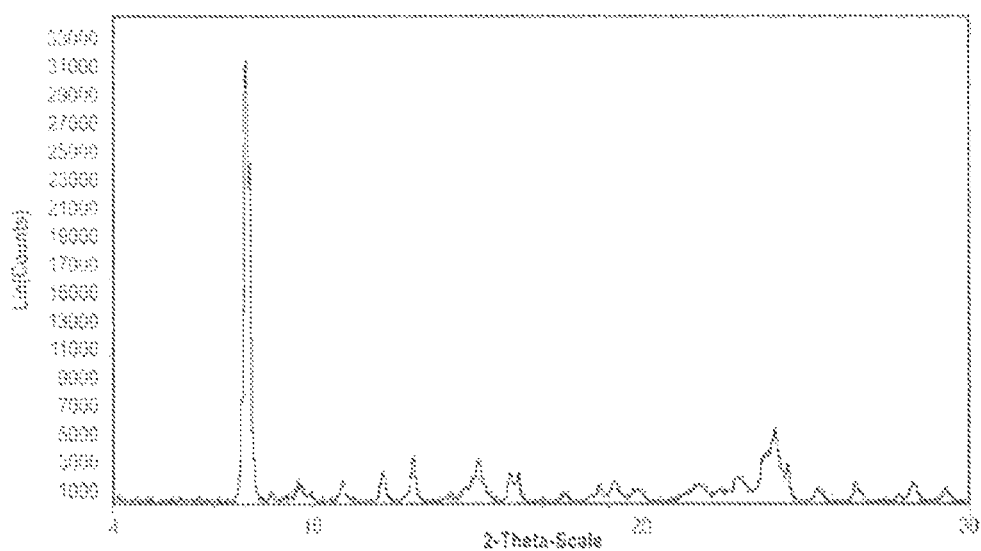

Figure 11: XRPD pattern of form 6 which is described PCT application WO2017011399.
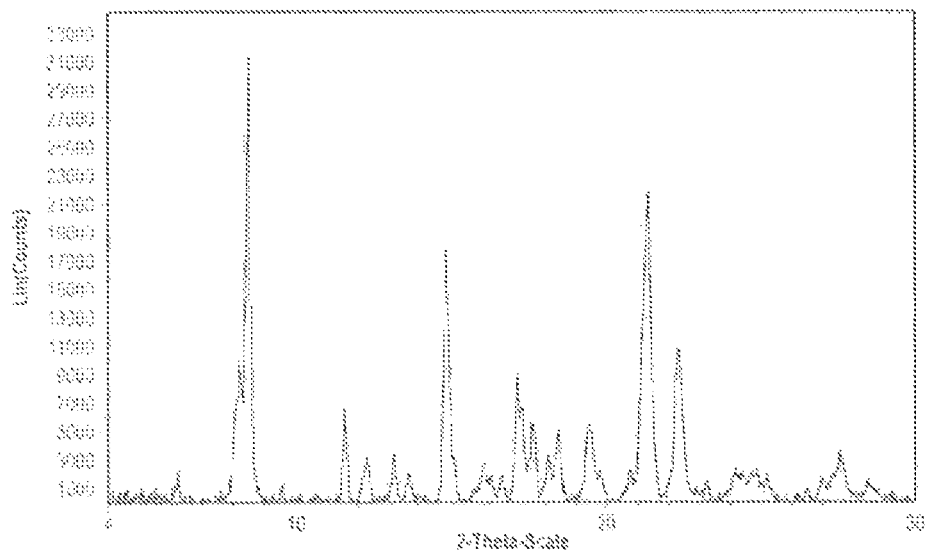
Figure 12: XRPD pattern of Plinabulin Form H obtained in Example 10.
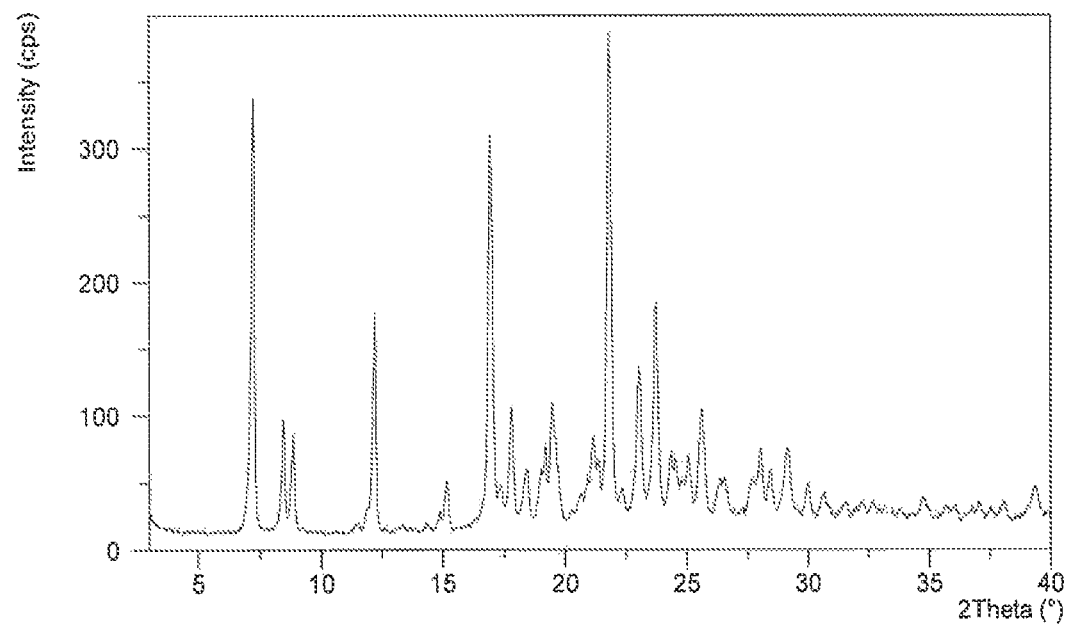

Figure 13: XRPD pattern of Plinabulin Form J (measured with internal Si standard) obtained in Example 11.
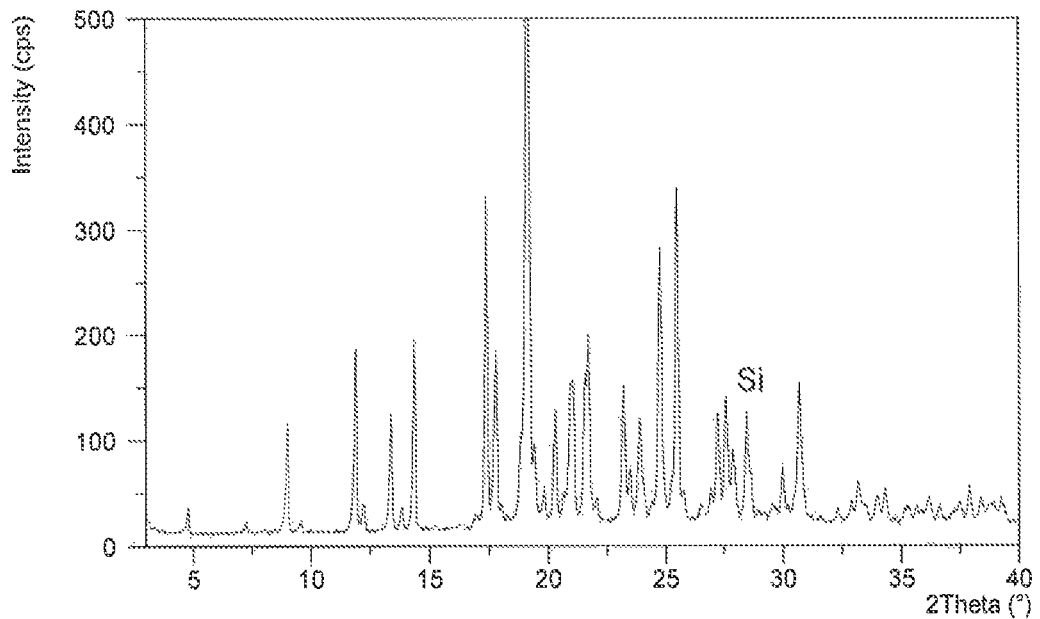
Figure 14: XRPD pattern of Plinabulin Form K obtained in Example 12.
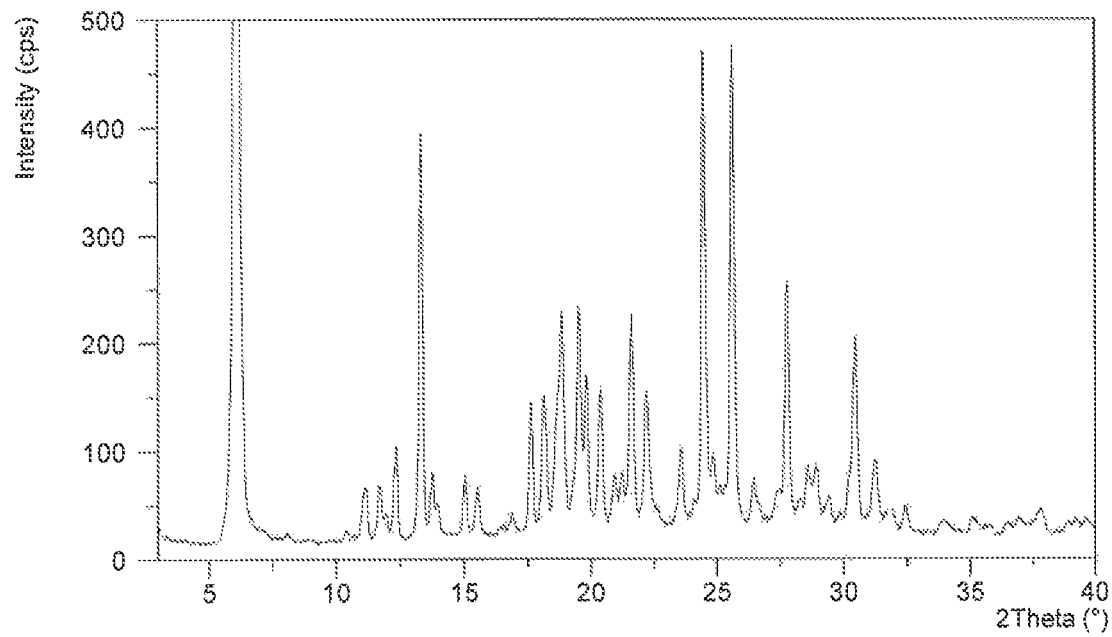

Figure 15: XRPD pattern of Amorphous Plinabulin obtained in Example 13 (The origin of the small peak at about 32.6 degrees two theta might be related to unknown inorganic impurity)
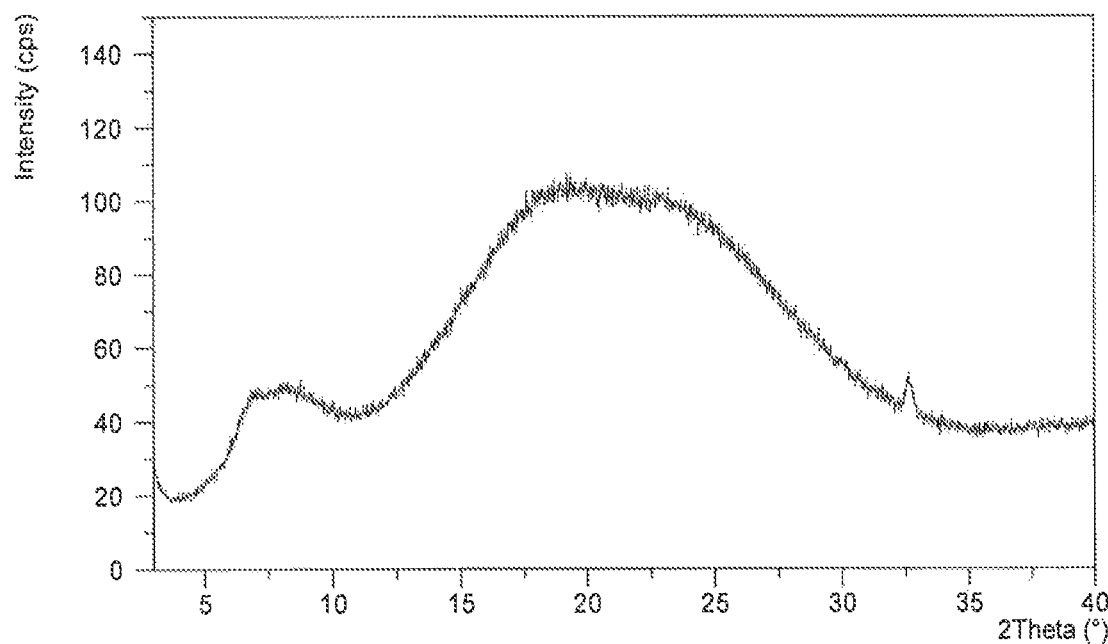
Figure 16: XRPD pattern of Plinabulin Form T obtained in Example 14
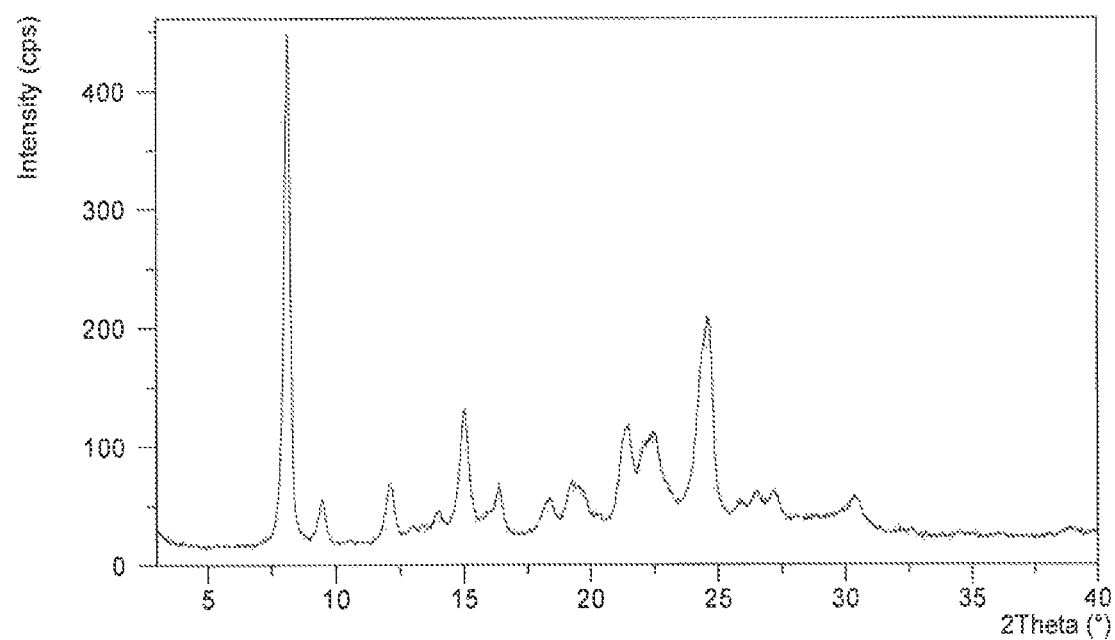

Figure 17: Solid state $^{13}$C NMR spectrum of Form G of Plinabulin at the range of 200-0 ppm.
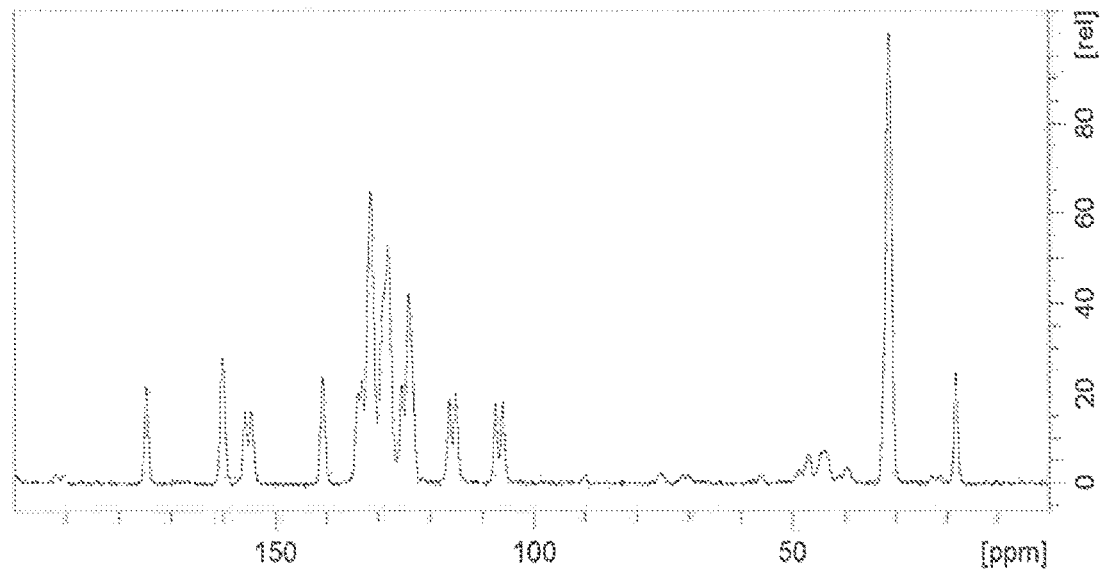
Figure 18: Solid state 13C NMR spectrum of Form G of Plinabulin at the range of 200-100 ppm.
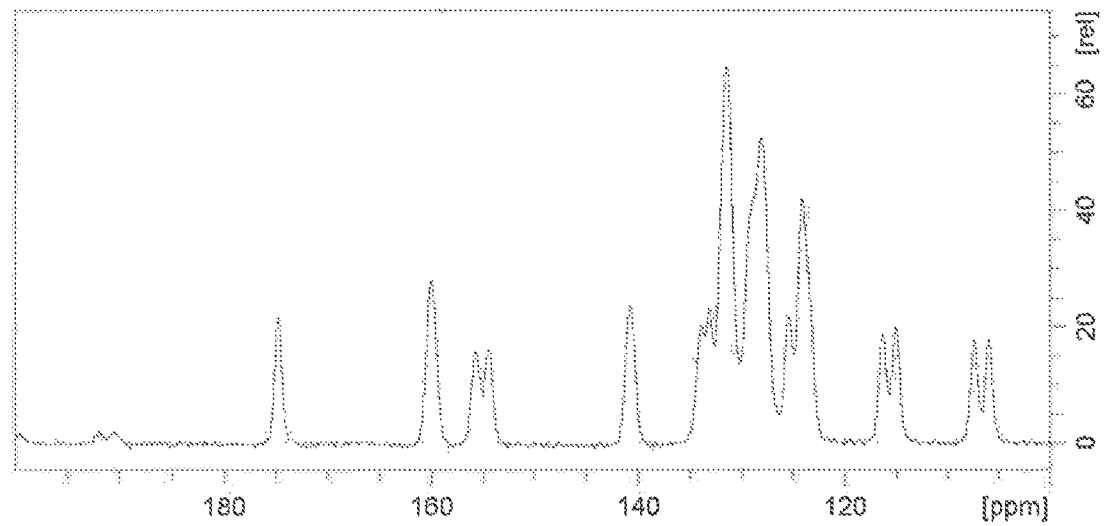

Figure 19: Solid state 13C NMR spectrum of Form G of Plinabulin at the range of 100-0 ppm.
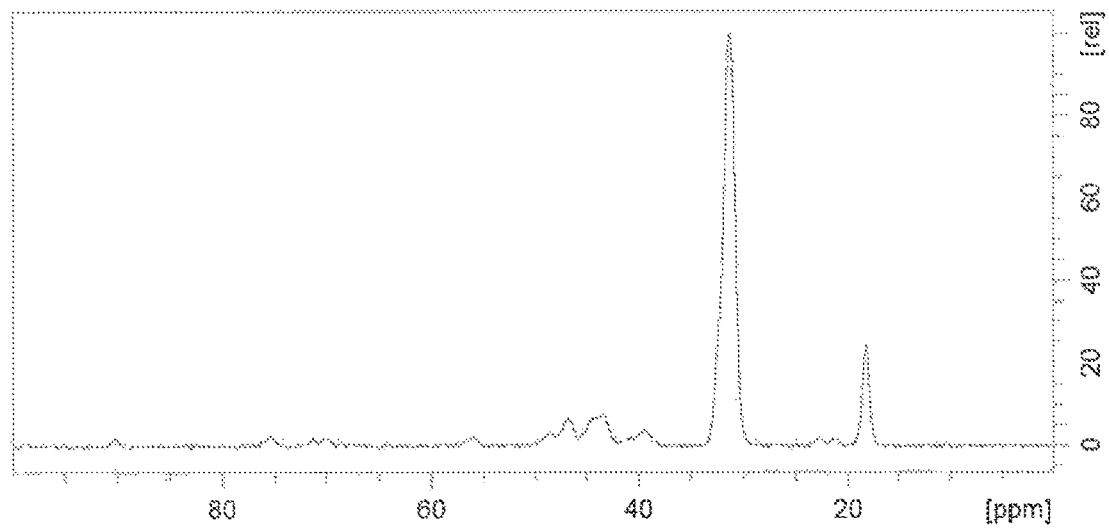
Figure 20: A Fourier-transform infrared (FTIR) spectrum of Plinabulin Form G at the range of 400-4000 cm-1.
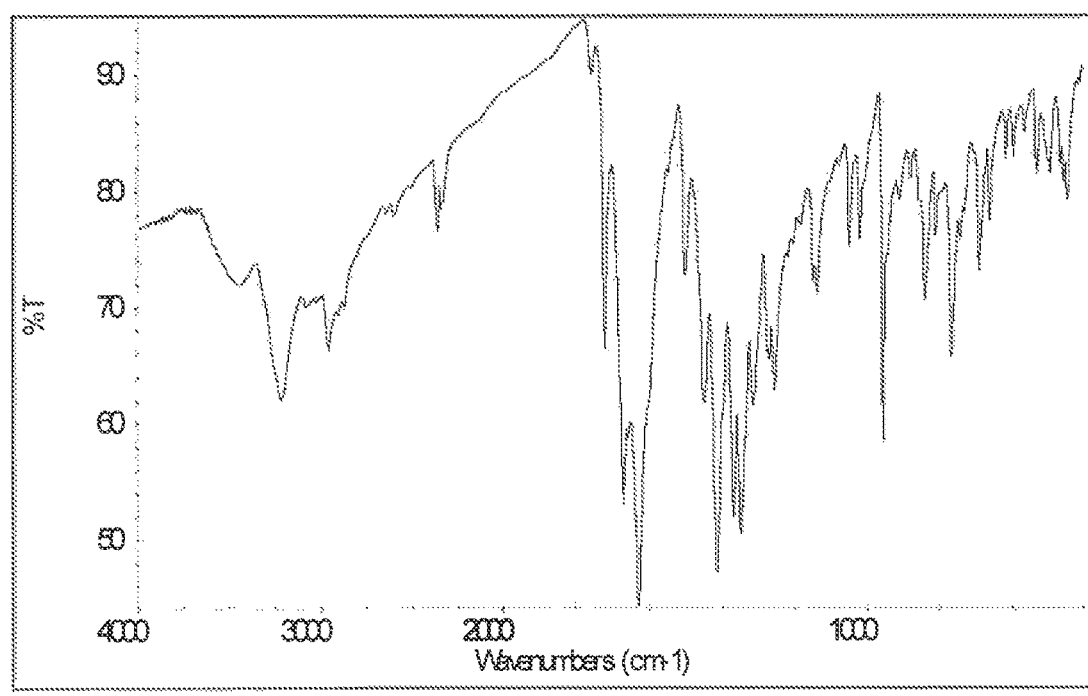

Figure 21: A Fourier-transform infrared (FTIR) spectrum of Plinabulin Form G at the range of 400-1800 cm-1.
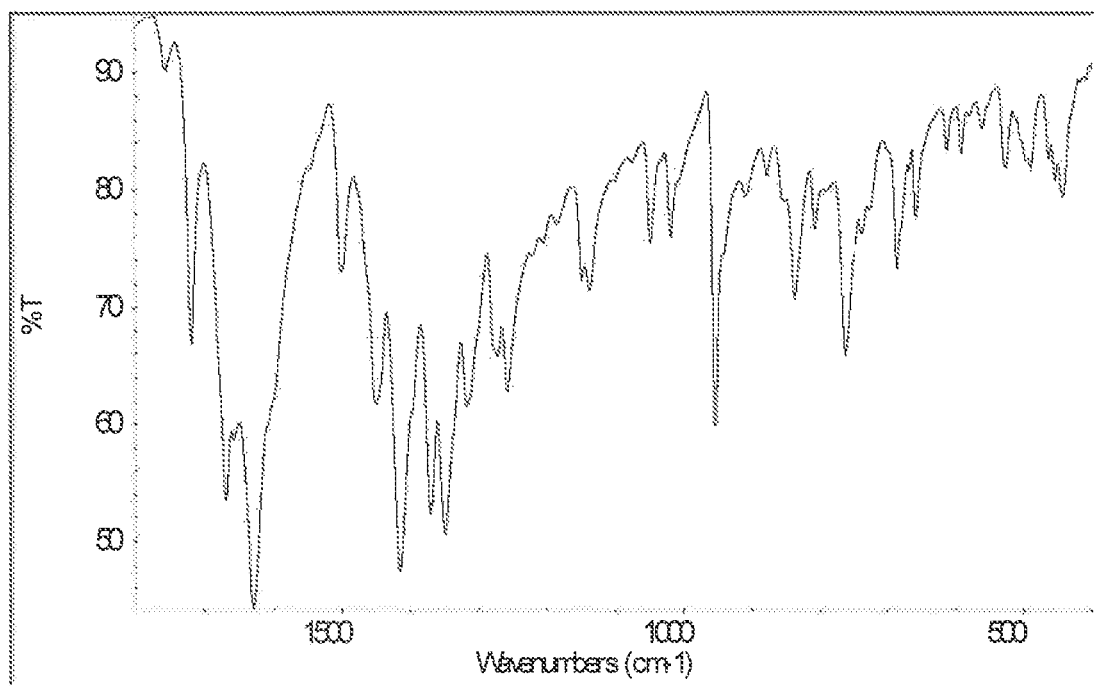
Figure 22: FT-Raman spectrum of Plinabulin Form G at the range of 400-4000 cm-1.
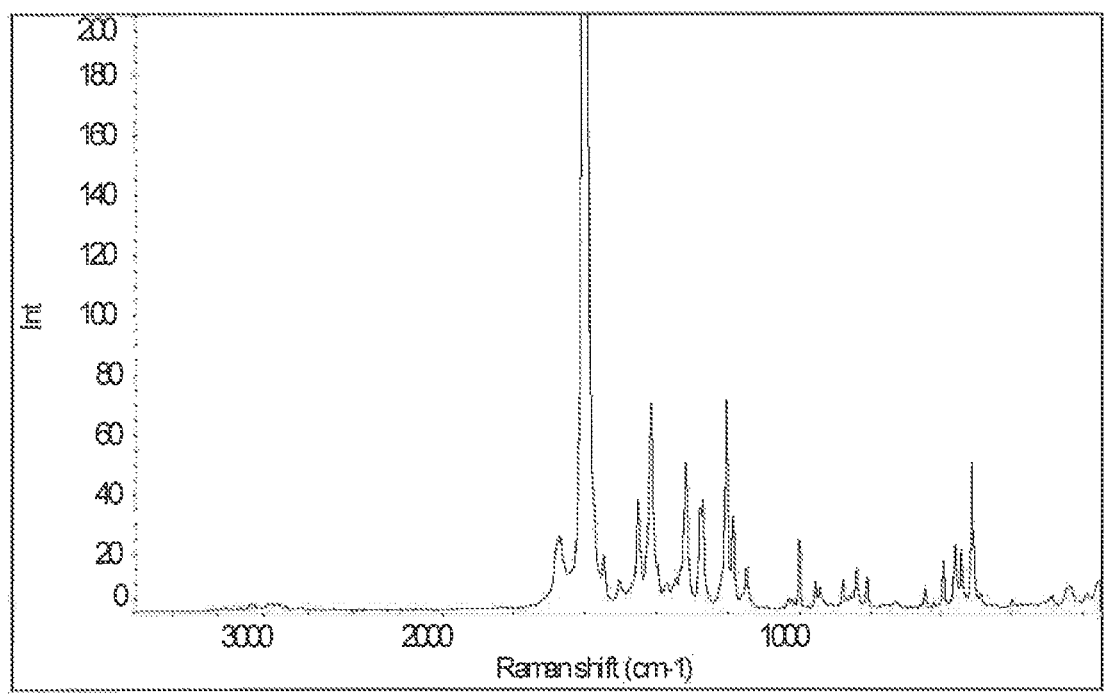

Figure 23: FT-Raman spectrum of Plinabulin Form G at the range of 400-2000 cm-1.
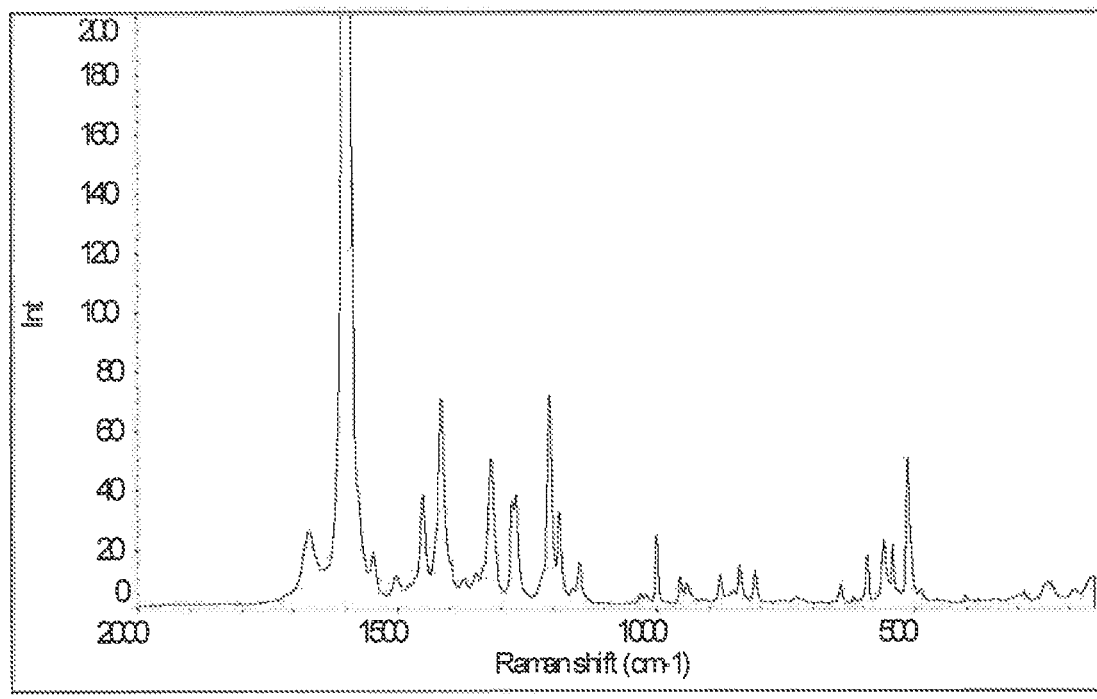
Figure 24: Solid state 13C NMR spectrum of Plinabulin hydrochloride Form Alpha at the range of 200-0 ppm.
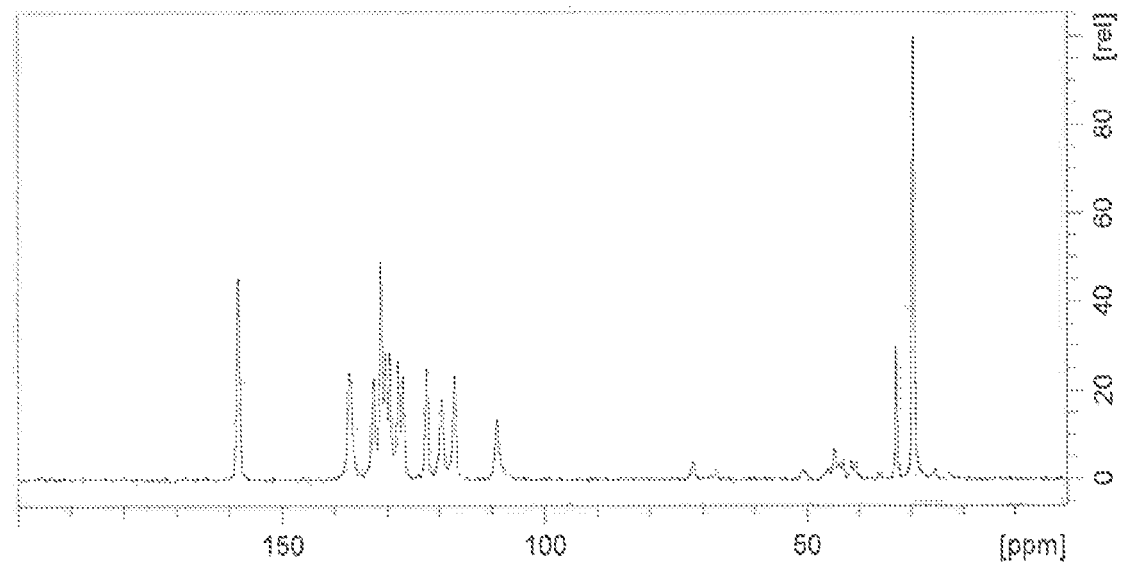

Figure 25: Solid state 13C NMR spectrum of Plinabulin hydrochloride Form Alpha at the range of 200-100 ppm.
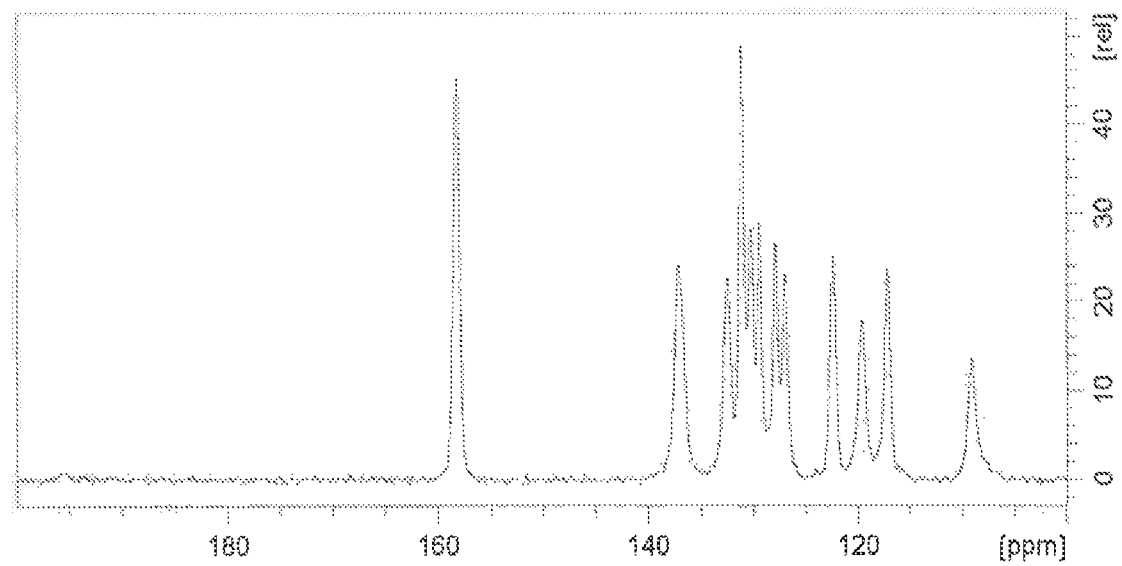
Figure 26: Solid state 13C NMR spectrum of Plinabulin hydrochloride Form Alpha at the range of 100-0 ppm.
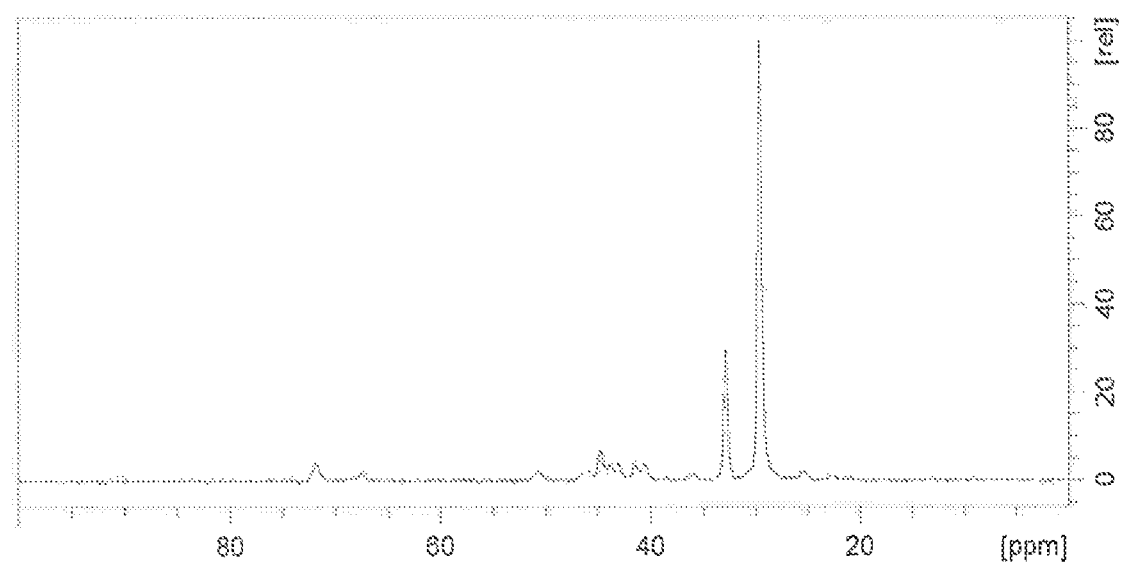

Figure 27: Fourier-transform infrared (FTIR) spectrum of Plinabulin hydrochloride Form Alpha at the range of 400-4000 cm-1.
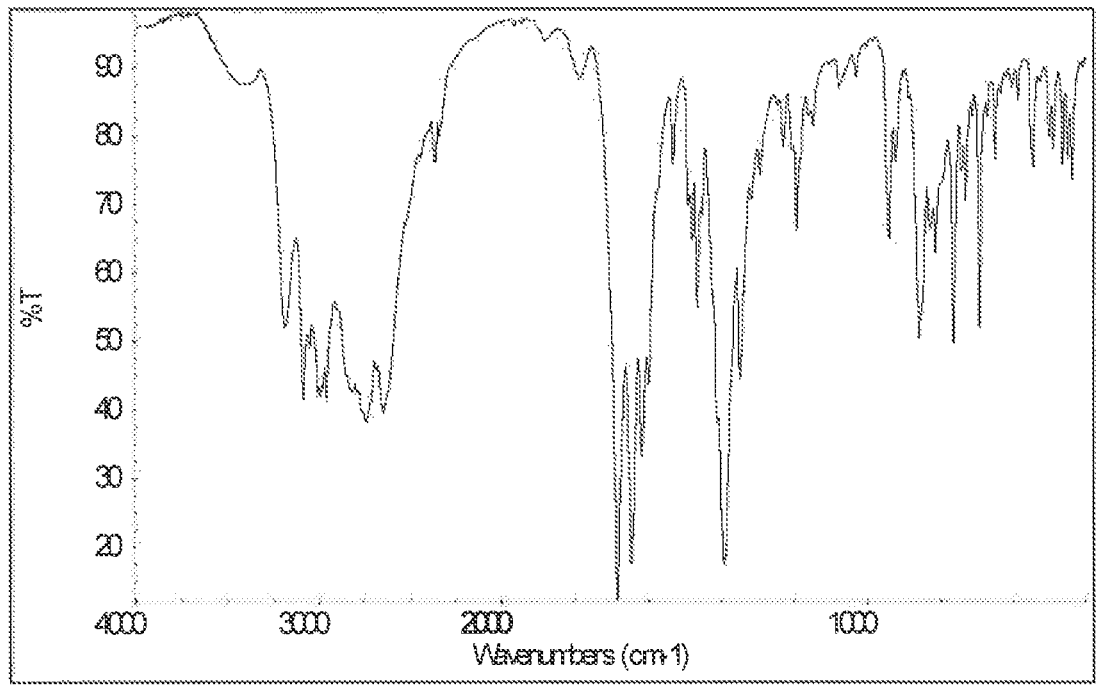
Figure 28: Fourier-transform infrared (FTIR) spectrum of Plinabulin hydrochloride Form Alpha at the range of 400-1800 cm-1.
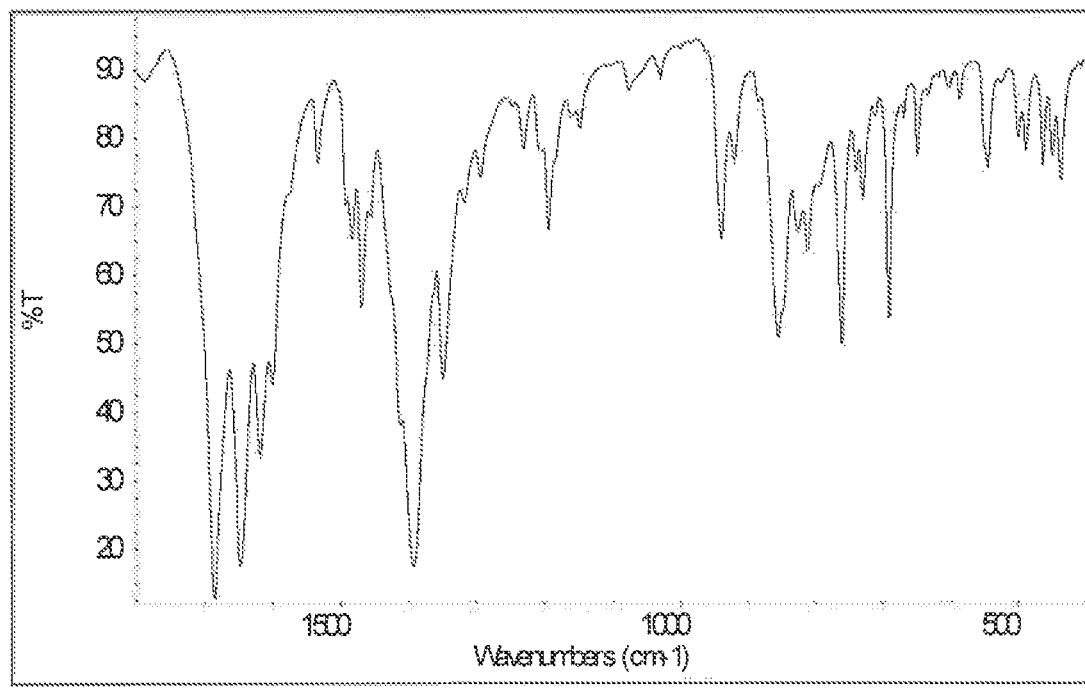

Figure 29: A FT-Raman spectrum of Plinabulin hydrochloride Form Alpha at the range of 400-4000 cm-1.
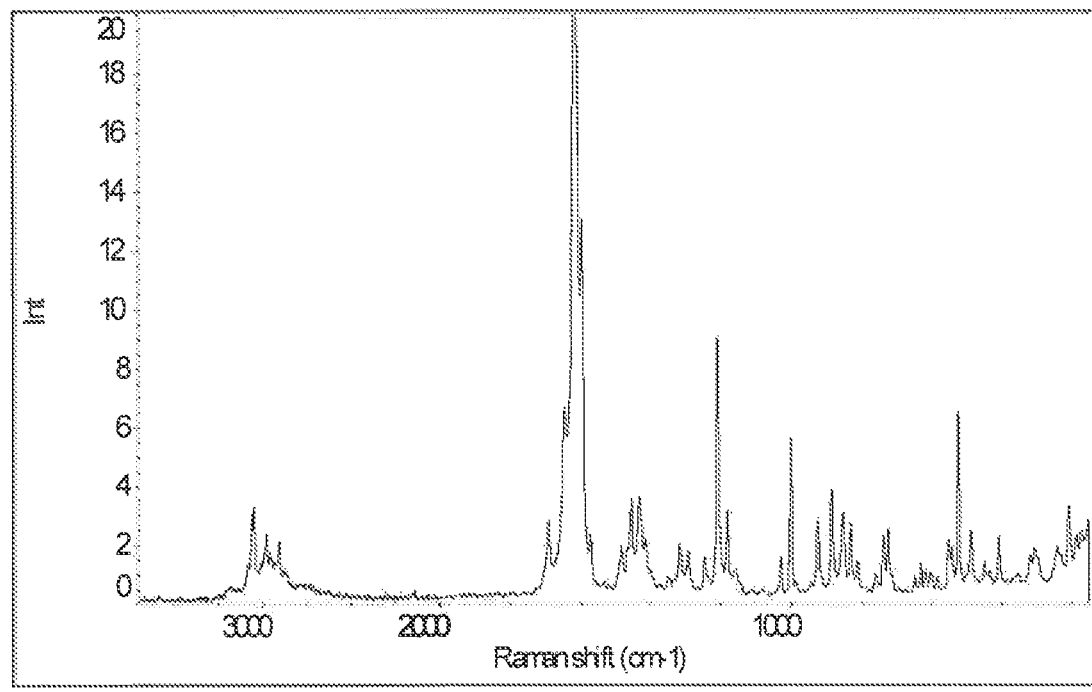
Figure 30: FT-Raman spectrum of Plinabulin hydrochloride Form Alpha at the range of 400-2000 cm-1.
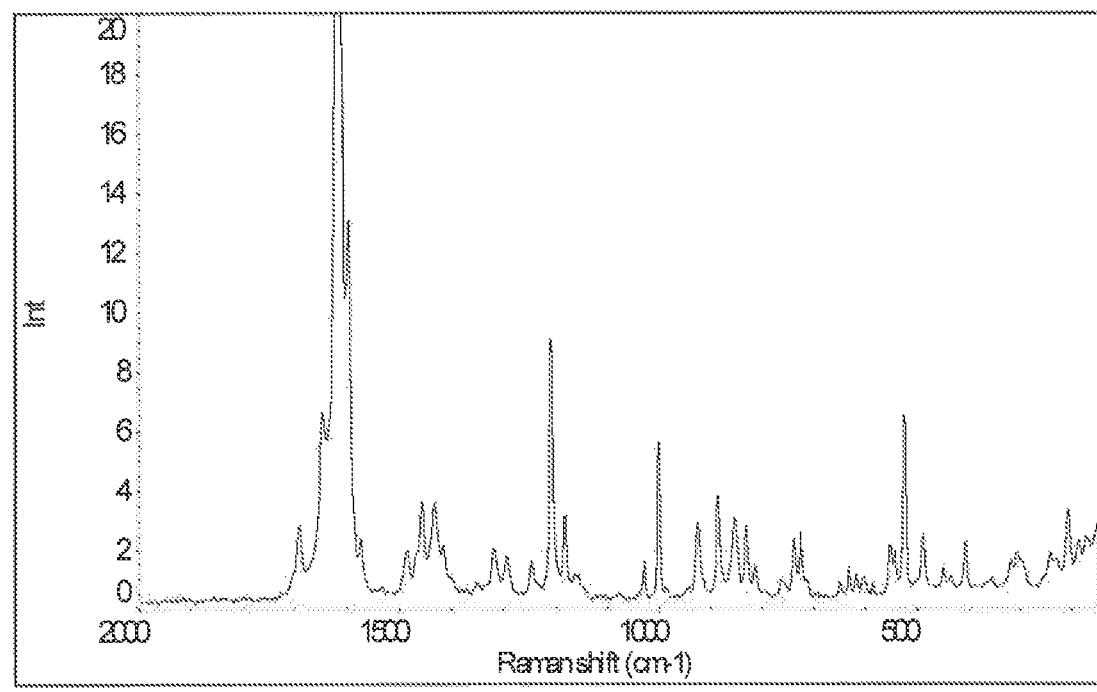

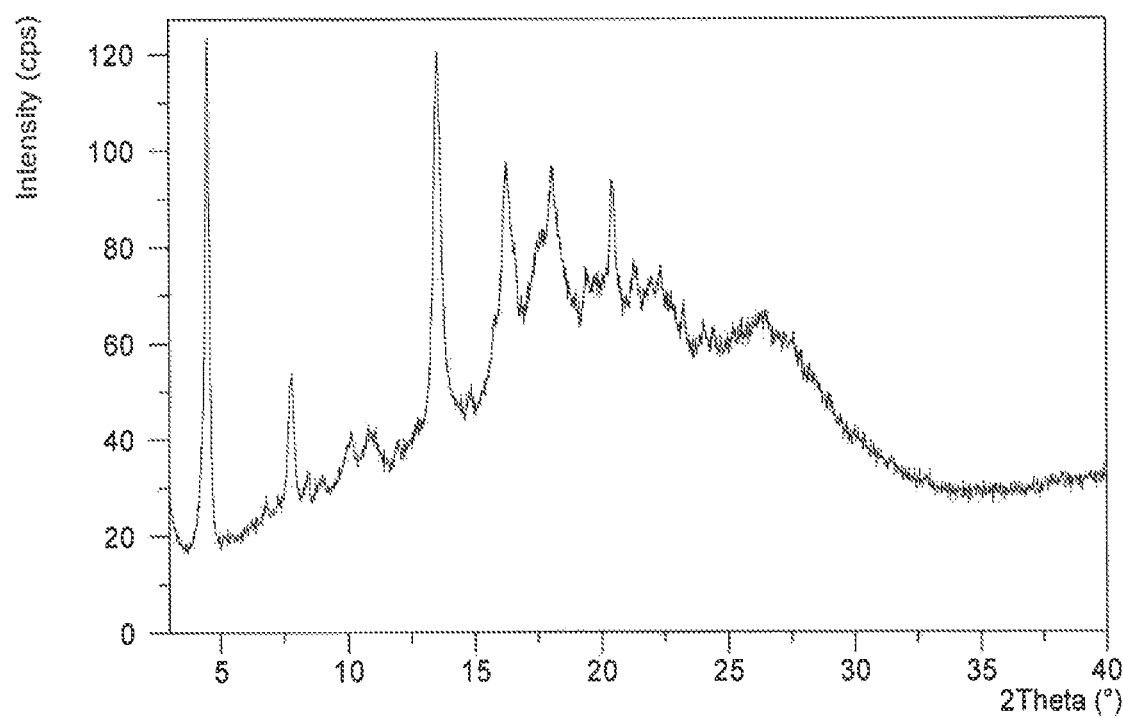
Figure 31. XRPD pattern of Plinabulin Form U obtained in Example 15

SALTS AND SOLID STATE FORMS OF PLINABULIN

CROSS REFERENCE TO RELATED APPLICATIONS AS FOLLOWS

This application is a National Stage of, and claims priority to and the benefit of, International Patent Application No. PCT/US2018/044815 filed on Aug. 1, 2018, which, in turn, claims the benefit of, and priority to, U.S. Provisional Patent Application Ser. Nos. 62/540,653 filed Aug. 3, 2017, 62/563,825 filed Sep. 27, 2017 and 62/586,239 filed Nov. 15, 2017, the entire disclosures of each of which are incorporated by reference herein.

FIELD OF THE INVENTION

The present disclosure relates to Plinabulin solid state forms, Plinabulin salts including hydrochloride and solid state forms thereof, processes for preparation thereof, pharmaceutical compositions thereof, and methods of use thereof.

BACKGROUND

Plinabulin (KPU-02) which has the chemical name (3Z,6Z)-3-Benzylidene-6-{[5-(2-methyl-2-propanyl)-1H-imidazol-4-yl]methylene}-2,5-piperazinedione is a small molecule diketopiperazine derived from a marine fungus of the *Aspergillus* species, as an IV tumour vascular disrupting (VDA) agent. The drug induces dendritic cell maturation and generates an amplified immune response to the cancer. As described in U.S. Pat. No. 7,064,201, Plinabulin (KPU-02) has the following chemical structure:

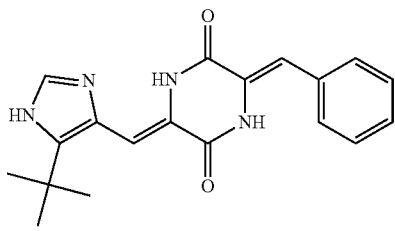 [SMILES: CC(C)(C)c1[nH]cnc1/C=c1\[nH]c(=O)/c(=C/c2ccccc2)[nH]c1=O]

Plinabulin preparation is disclosed in U.S. Pat. No. 7,064,201. Solid state forms of Plinabulin, forms 1-9, are disclosed in PCT application WO2017/011399. Solid state forms of Plinabulin are also described in PCT application WO2018/028420.

Polymorphism, the occurrence of different crystal forms, is a property of some molecules and molecular complexes. A single compound, like Plinabulin, may give rise to a variety of polymorphs having distinct crystal structures and physical properties like melting point, thermal behaviors (e.g. measured by thermogravimetric analysis—"TGA", or differential scanning calorimetry—"DSC"), X-ray powder diffraction (XRPD) pattern, infrared absorption fingerprint, Raman absorption fingerprint, and solid state ($^{13}$C—) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, improving the dissolution profile, or improving stability (polymorph as well as chemical stability) and shelf-life. These variations in the properties of different salts and solid state forms may also provide improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new salts and solid state forms and solvates of a pharmaceutical product can provide materials having desirable processing properties, such as ease of handling, ease of processing, storage stability, and ease of purification or as desirable intermediate crystal forms that facilitate conversion to other salts or polymorphic forms. New polymorphic forms and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life. For at least these reasons, there is a need for additional salts and solid state forms (including solvated forms) of Plinabulin.

SUMMARY OF THE INVENTION

The present disclosure relates to Plinabulin solid state forms, Plinabulin salts including hydrochloride and solid state forms thereof, to processes for preparation thereof, and to pharmaceutical compositions comprising these salts and solid state forms.

In particular the present disclosure provides crystalline forms of Plinabulin designated as Forms A-H, J-K, T and U (defined herein) and crystalline form of Plinabulin hydrochloride salt designated as Form Alpha (defined herein).

The present disclosure further provides process for preparing Plinabulin and Plinabulin hydrochloride solid state forms thereof.

The present disclosure also relates to the uses of any one or a combination of the solid state forms of Plinabulin, Plinabulin salts, including hydrochloride and solid state form thereof of the present disclosure, for preparing other solid state forms of Plinabulin and Plinabulin salts, such as hydrochloride salt of Plinabulin and solid state thereof.

The present disclosure also relates to any one or a combination of the above described solid state forms of Plinabulin and Plinabulin salts, including hydrochloride of the present disclosure, for use in preparing other solid state forms of Plinabulin and Plinabulin salts, such as hydrochloride salt, and solid state forms thereof.

In another aspect, the present disclosure encompasses the above described solid state forms of Plinabulin, Plinabulin salts, including hydrochloride, and solid state form thereof for use in the preparation of pharmaceutical compositions and/or formulations for use in medicine, preferably for treating cancer, such as breast, sarcoma, colon and prostate cancers.

The present disclosure also encompasses the uses of the above described solid state forms of Plinabulin and solid state forms of Plinabulin salts, including hydrochloride, for the preparation of pharmaceutical compositions and/or formulations, preferably for use in medicine, preferably for treating cancer, such as breast, sarcoma, colon and prostate cancers.

In yet another embodiment, the present disclosure encompasses pharmaceutical compositions comprising any one or a mixture of the solid state forms of Plinabulin and Plinabulin salts, including hydrochloride.

In yet another embodiment, the present disclosure encompasses pharmaceutical formulations comprising solid state forms of Plinabulin and solid state forms of Plinabulin salts, such as hydrochloride, when the pharmaceutical formulation comprising the solid state forms of Plinabulin and/or salts of Plinabulin, and at least one pharmaceutically acceptable excipient.

The present disclosure further encompasses processes to prepare said pharmaceutical formulations of Plinabulin comprising combining any one of the above described salts and solid state forms of Plinabulin, or pharmaceutical compositions comprising them, and at least one pharmaceutically acceptable excipient.

The salts and solid state forms as defined herein as well as the pharmaceutical compositions or formulations of the salts and the solid state form of Plinabulin can be used as medicaments, particularly for treating cancer. The present disclosure encompasses a method of treating cancer comprising administering a therapeutically effective amount of any of the solid state form and/or salt of the present disclosure, or at least one of the above pharmaceutical compositions or formulations, to a subject suffering from cancer, or otherwise in need of the treatment.

The present disclosure also provides the uses of the solid state forms of Plinabulin and salts thereof of the present disclosure, or at least one of the above pharmaceutical compositions or formulations, for the manufacture of medicaments for treating cancer.

BRIEF DESCRIPTION OF THE DRAWINGS

FIG. 1 shows an X-ray powder diffraction (XRPD) pattern of Form A of Plinabulin.
FIG. 2 shows an XRPD pattern of Form B of Plinabulin.
FIG. 3 shows an XRPD pattern of Form C of Plinabulin.
FIG. 4 shows an XRPD pattern of Form D of Plinabulin.
FIG. 5 shows an XRPD pattern of Form E of Plinabulin.
FIG. 6 shows an XRPD pattern of Form F of Plinabulin.
FIG. 7 shows an XRPD pattern of Form G of Plinabulin.
FIG. 8 shows an XRPD pattern of form Alpha of Plinabulin hydrochloride salt.
FIG. 9 shows the XRPD pattern of form 1 which is described in PCT application WO2017011399.
FIG. 10 shows the XRPD pattern of form 5 which is described in PCT application WO2017011399.
FIG. 11 shows the XRPD pattern of form 6 which is described PCT application WO2017011399.
FIG. 12 shows the XRPD pattern of Form H of Plinabulin.
FIG. 13 shows the XRPD pattern of Form J of Plinabulin.
FIG. 14 shows the XRPD pattern of Form K of Plinabulin.
FIG. 15 shows an XRPD pattern of Amorphous Plinabulin.
FIG. 16 shows an XRPD pattern of Plinabulin Form T.
FIG. 17 shows solid state $^{13}$C-NMR spectrum of form G of Plinabulin at the range of 200-0 ppm.
FIG. 18 shows solid state $^{13}$C-NMR spectrum of form G of Plinabulin at the range of 200-100 ppm.
FIG. 19 shows solid state $^{13}$C-NMR spectrum of form G of Plinabulin at the range of 100-0 ppm.

FIG. 20 shows a Fourier-transform infrared (FTIR) spectrum of Plinabulin Form G at the range of 400-4000 cm-1.
FIG. 21 shows a Fourier-transform infrared (FTIR) spectrum of Plinabulin Form G at the range of 400-1800 cm-1.
FIG. 22 shows a FT-Raman spectrum of Plinabulin Form G at the range of 400-4000 cm-1.
FIG. 23 shows a FT-Raman spectrum of Plinabulin Form G at the range of 400-2000 cm-1.
FIG. 24 shows solid state $^{13}$C-NMR spectrum of Plinabulin hydrochloride Form Alpha at the range of 200-0 ppm.
FIG. 25 shows solid state $^{13}$C-NMR spectrum of Plinabulin hydrochloride Form Alpha at the range of 200-100 ppm.
FIG. 26 shows solid state $^{13}$C-NMR spectrum of Plinabulin hydrochloride Form Alpha at the range of 100-0 ppm.
FIG. 27 shows a Fourier-transform infrared (FTIR) spectrum Plinabulin hydrochloride Form Alpha at the range of 400-4000 cm-1
FIG. 28 shows a Fourier-transform infrared (FTIR) spectrum of Plinabulin hydrochloride Form Alpha at the range of 400-1800 cm-1
FIG. 29 shows a FT-Raman spectrum of Plinabulin hydrochloride Form Alpha at the range of 400-4000 cm-1.
FIG. 30 shows a FT-Raman spectrum of Plinabulin hydrochloride Form Alpha at the range of 400-2000 cm-1.
FIG. 31 shows the XRPD pattern of Form U of Plinabulin.

DETAILED DESCRIPTION OF ILLUSTRATIVE EMBODIMENTS

The present disclosure relates to solid state forms of Plinabulin, salts of Plinabulin, including hydrochloride, and solid state thereof, to processes for preparation thereof and to pharmaceutical compositions comprising solid state forms and salts and/or combinations thereof. The disclosure also relates to the conversion of the Plinabulin to other salt and/or to other solid state form of Plinabulin.

The Plinabulin solid state forms, Plinabulin salts, including hydrochloride, and solid state thereof according to the present disclosure may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents, adhesive tendencies and advantageous processing and handling characteristics such as compressibility, and bulk density.

A crystal form may be referred to herein as being characterized by graphical data "as depicted in" a Figure. Such data include, for example, powder X-ray diffractograms (PXRD) and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

A crystal form of Plinabulin or a salt thereof referred to herein as being characterized by graphical data "as depicted in" a Figure will thus be understood to include any crystal forms of Plinabulin or a salt thereof, characterized with the graphical data having such small variations, as are well known to the skilled person, in comparison with the Figure.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% (w/w) of any other forms of the subject compound as measured, for example, by XRPD. Thus, solid states of Plinabulin or a salt thereof described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject salts or solid state form of Plinabulin. Accordingly, in some embodiments of the disclosure, the described salts and solid state forms of Plinabulin may contain from about 1% to about 20% (w/w), from about 5% to about 20% (w/w), or from about 5% to about 10% (w/w) of one or more solid state forms of Plinabulin or salts thereof.

As used herein unless stated otherwise, reference to % values are to wt % (This is based on an assumption that the solvent % in the various forms is measured in wt %).

As used herein, unless stated otherwise, XRPD peaks reported herein are preferably measured using CuKα radiation, λ=1.54187 A, preferably, XRPD peaks reported herein are measured using CuK α radiation, λ=1.54187 Å, at a temperature of 25±3° C.

As used herein, unless stated otherwise, $^{13}$C solid state NMR was measured on 400 MHz at room temperature using a spin rate of 11 kHz.

As used herein, unless stated otherwise, Fourier-transform infrared (FTIR) was measured using KBr pellet at the range of 400-4000 cm'.

As used herein, unless stated otherwise, FT-Raman was measured with FT-Raman module, equipped with 1064 nm at the range of 3700-150 cm'.

As used herein, unless stated otherwise, TGA was carried out using heating rate of 10° C./min.

As used herein, the term "isolated" in reference to solid state forms and salts of Plinabulin of the present disclosure corresponds to salt and solid state form of Plinabulin that is physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

A process or step may be referred to herein as being carried out "overnight." This refers to a time interval, e.g., for the process or step, that spans the time during the night, when that process or step may not be actively observed. This time interval is from about 8 to about 20 hours, or about 10 to about 18 hours, typically about 16 hours.

As used herein, the expression "wet crystalline form" refers to a polymorph that was not dried using any conventional techniques to remove residual solvent. Examples for such conventional techniques can be, but not limited to, evaporation, vacuum drying, oven drying, drying under nitrogen flow, and the like.

As used herein, the expression "dry crystalline form" refers to a polymorph that was dried using any conventional techniques to remove residual solvent. Examples of such conventional techniques can be, but are not limited to, evaporation, vacuum drying, oven drying, drying under nitrogen flow, and the like.

As used herein, and unless stated otherwise, the term "anhydrous" in relation to crystalline Plinabulin or a salt thereof which does not include any crystalline water (or other solvents) in a defined, stoichiometric amount or in non-defined amount within the crystal. Moreover, an "anhydrous" form does not contain more than about 1% (w/w) of either water or organic solvents as measured for example by TGA, Karl Fischer or by other suitable technique.

The term "solvate", as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount. Stoichiometric of one water molecule within the crystal structure is defined as a "monohydrate".

The amount of solvent employed in a chemical process, e.g., a reaction or crystallization may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding (methyl tert-butyl ether) MTBE (1.5 v/v) to a 100 ml reaction mixture would indicate that 150 mL of MTBE was added.

As used herein the term non-hygroscopic in relation to crystalline Plinabulin or a salt thereof, refers to less than about 1.0% (w/w) absorption of water at about 25° C. and about 80% relative humidity (RH), as determined for example by TGA or other suitable technique.

As used herein, the term "reduced pressure" refers to a pressure of about 10 mbar to about 500 mbar.

As used herein, and unless indicated otherwise, the term "thermo-dynamical stability" in relation to solid state forms of Plinabulin and salts thereof refers to resistance of the solid state form to polymorphic conversion under certain conditions, for example, heating, melting or dissolving. In some embodiments, the term refers to less than about 20% (w/w), about 10% (w/w), about 5% (w/w), about 1% (w/w), about 0.5% (w/w), or about 0% (w/w) conversion of crystalline Plinabulin or a salt thereof to any other solid state form of Plinabulin or a salt thereof as measured by XRPD. In some embodiments, the conversion is about 1% (w/w) to about 20% (w/w), about 1% (w/w) to about 10% (w/w) or about 1% (w/w) to about 5% (w/w).

As used therein the terms "form 1", "form 5" and "form 6" of Plinabulin relates to crystalline forms, having an XRPD pattern shown herein in FIGS. 9-11, as described in PCT application WO2017011399.

The present disclosure comprises a crystalline form of Plinabulin designated as Form A. The crystalline Form A of Plinabulin can be characterized by data selected from one or more of the following: an XRPD pattern having peaks at 7.4, 11.4, 12.2, 14.9 and 27.4 degrees 2-theta±0.2 degrees 2-theta; an XRPD pattern substantially as depicted in FIG. 1; or combinations of these data. Crystalline Form A of Plinabulin may be further characterized by data selected from one or more of the following: an XRPD pattern having peaks at 7.4, 11.4, 12.2, 14.9 and 27.4 degrees two theta±0.2 degrees two theta; and also having one, two, three, four or five additional peaks selected from 9.4, 15.6, 18.7, 23.3 and 24.1 degrees two theta±0.2 degrees two theta.

Crystalline Form A may alternatively be characterized by an XRPD pattern having peaks at 7.4, 9.4, 11.4, 12.2, 14.9, 15.6, 18.7, 23.3, 24.1 and 27.4 degrees two theta±0.2 degrees two theta.

Crystalline Form A of Plinabulin may be characterized by each of the above characteristics alone/or by all possible combinations, e.g. by XRPD pattern having peaks at 7.4, 11.4, 12.2, 14.9 and 27.4 degrees 2-theta±0.2 degrees 2-theta and an XRPD pattern as depicted in FIG. 1. In certain embodiments, crystalline Plinabulin Form A may optionally be characterized as a DMF solvate.

The present disclosure further comprises a crystalline form of Plinabulin designated as Form B. The crystalline Form B of Plinabulin can be characterized by data selected from one or more of the following: an XRPD pattern having peaks at 6.1, 13.7, 13.9, 20.9 and 27.1 degrees two theta±0.2 degrees two theta; an XRPD pattern substantially as depicted in FIG. 2; or combinations of these data. Crystalline Form B of Plinabulin may be further characterized by data selected from one or more of the following: an XRPD pattern having peaks at 6.1, 13.7, 13.9, 20.9 and 27.1 degrees two theta±0.2 degrees two theta; and also having one, two, three, four or five additional peaks selected from 17.5, 17.8, 18.4, 22.1 and 25.1 degrees two theta±0.2 degrees two theta.

Crystalline Form B may alternatively be characterized by an XRPD pattern having peaks at 6.1, 13.7, 13.9, 17.5, 17.8, 18.4, 20.9, 22.1, 25.1 and 27.1 degrees two theta±0.2 degrees two theta.

Crystalline Form B of Plinabulin may be characterized by each of the above characteristics alone/or by all possible combinations, e.g. by XRPD pattern having peaks at 6.1, 13.7, 13.9, 20.9 and 27.1 degrees two theta±0.2 degrees two theta and an XRPD pattern as depicted in FIG. 2. In certain embodiments, crystalline Plinabulin Form B may be optionally characterized as a trifluoroethanol solvate. In certain embodiments, form B may contain from about 21% to about 25% by weight of trifluoroethanol, specifically about 22.9% of trifluoroethanol.

The present disclosure also comprises a crystalline form of Plinabulin designated as Form C. The crystalline Form C of Plinabulin can be characterized by data selected from one or more of the following: an XRPD pattern having peaks at 5.4, 6.7, 7.8, 11.6 and 14.3 degrees two theta±0.2 degrees two theta; an XRPD pattern substantially as depicted in FIG. 3; or combinations of these data. Crystalline Form C of Plinabulin may be further characterized by data selected from one or more of the following: an XRPD pattern having peaks at 5.4, 6.7, 7.8, 11.6 and 14.3 degrees two theta±0.2 degrees two theta; and also having one, two, three, four or five additional peaks selected from 13.5, 15.4, 17.2, 22.2 and 25.6 degrees two theta±0.2 degrees two theta.

Crystalline Form C may alternatively be characterized by an XRPD pattern having peaks at 5.4, 6.7, 7.8, 11.6, 13.5, 14.3 15.4, 17.2, 22.2 and 25.6 degrees two theta±0.2 degrees two theta.

Crystalline Form C of Plinabulin may be characterized by each of the above characteristics alone/or by all possible combinations, e.g. by XRPD pattern having peaks at 5.4, 6.7, 7.8, 11.6 and 14.3 degrees two theta±0.2 degrees two theta and an XRPD pattern as depicted in FIG. 3. In some embodiments, crystalline Plinabulin Form C may be optionally characterized as a trifluoroethanol solvate, preferably hemisolvate of trifluoroethanol. In certain embodiments, form C may contain from about 10% to about 15% by weight of trifluoroethanol, specifically about 13% of trifluoroethanol.

The present disclosure also comprises a crystalline form of Plinabulin designated as Form D. The crystalline Form D of Plinabulin can be characterized by data selected from one or more of the following: an XRPD pattern having peaks at 8.3, 9.1, 10.1, 20.9 and 22.3 degrees two theta±0.2 degrees two theta; an XRPD pattern substantially as depicted in FIG. 4; or combinations of these data. Crystalline Form D of Plinabulin may be further characterized by data selected from one or more of the following: an XRPD pattern having peaks at 8.3, 9.1, 10.1, 20.9 and 22.3 degrees two theta±0.2 degrees two theta; and also having one, two, three, four or five additional peaks selected from 11.8, 17.9, 18.5, 20.0 and 23.1 degrees two theta±0.2 degrees two theta.

Crystalline Form D may alternatively be characterized by an XRPD pattern having peaks at 8.3, 9.1, 10.1, 11.8, 17.9, 18.5, 20.0, 20.9, 22.3 and 23.1 degrees two theta±0.2 degrees two theta.

Crystalline Form D of Plinabulin may be characterized by each of the above characteristics alone/or by all possible combinations, e.g. by XRPD pattern having peaks at 8.3, 9.1, 10.1, 20.9 and 22.3 degrees two theta±0.2 degrees two theta and an XRPD pattern as depicted in FIG. 4. In some embodiments, crystalline Plinabulin Form D may be optionally characterized as a pyridine solvate.

The present disclosure further comprises a crystalline form of Plinabulin designated as Form E. The crystalline Form E of Plinabulin can be characterized by data selected from one or more of the following: an XRPD pattern having peaks at 7.0, 11.5, 13.4, 14.1 and 26.1 degrees two theta±0.2 degrees two theta; an XRPD pattern substantially as depicted in FIG. 5; or combinations of these data. Crystalline Form E of Plinabulin may be further characterized by data selected from one or more of the following: an XRPD pattern having peaks at 7.0, 11.5, 13.4, 14.1 and 26.1 degrees two theta±0.2 degrees two theta; and also having one, two, three, four or five additional peaks selected from 18.6, 19.5, 20.9, 21.0 and 23.2 degrees two theta±0.2 degrees two theta.

Crystalline Form E may alternatively be characterized by an XRPD pattern having peaks at 7.0, 11.5, 13.4, 14.1, 18.6, 19.5, 20.9, 21.0, 23.2 and 26.1 degrees two theta±0.2 degrees two theta.

Crystalline Form E of Plinabulin may be characterized by each of the above characteristics alone/or by all possible combinations, e.g. by XRPD pattern having peaks at 7.0, 11.5, 13.4, 14.1 and 26.1 degrees two theta±0.2 degrees two theta and an XRPD pattern as depicted in FIG. 5. In some embodiments, crystalline Plinabulin Form E may be optionally characterized as a morpholine solvate, preferably monosolvate of morpholine. In certain embodiments, form E may contain from about 19% to about 24% by weight of morpholine, specifically about 21% of morpholine.

The present disclosure further comprises a crystalline form of Plinabulin designated as Form F. The crystalline Form F of Plinabulin can be characterized by data selected from one or more of the following: an XRPD pattern having peaks at 6.4, 11.4, 11.8, 15.4 and 16.3 degrees two theta±0.2 degrees two theta; an XRPD pattern substantially as depicted in FIG. 6; or combinations of these data. Crystalline Form F of Plinabulin may be further characterized by data selected from one or more of the following: an XRPD pattern having peaks at 6.4, 11.4, 11.8, 15.4 and 16.3 degrees two theta±0.2 degrees two theta; and also having one, two, three, four or five additional peaks selected from 14.9, 18.7, 19.6, 23.2 and 24.3 degrees two theta±0.2 degrees two theta.

Crystalline Form F may alternatively be characterized by an XRPD pattern having peaks at 6.4, 11.4, 11.8, 14.9, 15.4, 16.3, 18.7, 19.6, 23.2 and 24.3 degrees two theta±0.2 degrees two theta.

Crystalline Form F of Plinabulin may be characterized by each of the above characteristics alone/or by all possible combinations, e.g. by XRPD pattern having peaks at 6.4, 11.4, 11.8, 15.4 and 16.3 degrees two theta±0.2 degrees two theta and an XRPD pattern as depicted in FIG. 6. In some embodiments, crystalline Plinabulin Form F may be optionally characterized as an N-methyl-morpholine solvate.

The present disclosure further comprises a crystalline form of Plinabulin designated as Form G. The crystalline Form G of Plinabulin can be characterized by data selected from one or more of the following: an XRPD pattern having peaks at 8.0, 10.6, 17.9, 18.2 and 24.8 degrees two theta±0.2 degrees two theta; an XRPD pattern substantially as depicted in FIG. 7; a solid-state $^{13}C$ NMR spectrum with signals at 174.7, 160.0, 140.7, 131.4 and 124.1 ppm±0.2 ppm; a solid state $^{13}C$ NMR spectrum having the following chemical shift absolute differences from a peak 105.9 ppm±1 ppm of 68.8, 54.1, 34.8, 25.5 and 18.1 ppm±0.1 ppm; a solid state $^{13}C$ NMR spectrum with signals at 174.7, 160.0, 154.5, 140.7, 131.4, 128.0, 124.1, 116.3, 115.0, 107.4, 105.9, 31.3 and 18.2 ppm±0.2 ppm; a solid-state $^{13}C$ NMR spectrum as depicted in FIG. 17 or 18 or 19; or combinations of these data. Crystalline Form G of Plinabulin may be characterized by each of the above characteristics alone/or by all possible combinations, e.g. by XRPD pattern having peaks at 8.0, 10.6, 17.9, 18.2 and 24.8 degrees two theta±0.2 degrees two theta and an XRPD pattern as depicted in FIG. 7.

Crystalline Form G of Plinabulin may be further characterized by data selected from one or more of the following: an XRPD pattern having peaks at 8.0, 10.6, 17.9, 18.2 and 24.8 degrees two theta±0.2 degrees two theta; and also having one, two, three, four or five additional peaks selected from 5.9, 11.4, 12.2, 13.1 and 15.2 degrees two theta±0.2 degrees two theta; an FTIR spectrum having peaks at 1670, 1659, 1631, 1452, 1416, 1371, 1350, 1318, 1258 and 955 cm$^{-1}$±4 cm$^{-1}$; an FTIR spectrum substantially as depicted in FIG. 20 or 21; an FT-Raman spectrum having peaks at 1673, 1600, 1453, 1417, 1320, 1273, 1207, 1189, 1000 and 513 cm$^{-1}$±4 cm$^{-1}$; an FT-Raman spectrum substantially as depicted in FIG. 22 or 23; or combinations of these data.

Crystalline Form G may alternatively be characterized by an XRPD pattern having peaks at 5.9, 8.0, 10.6, 11.4, 12.2, 13.1, 15.2, 17.9, 18.2 and 24.8 degrees two theta±0.2 degrees two theta.

In another embodiment crystalline Plinabulin Form G may be optionally characterized as an acetic acid solvate, preferably monoacetic acid solvate. In this embodiment, crystalline Plinabulin Form G may contain from about 7% to about 10% of acetic acid, preferably about 8% of acetic acid, as measured for example by TGA.

In one embodiment of the present disclosure, Form G is isolated.

In another embodiment of the present disclosure, Form G of Plinabulin is polymorphically pure.

As discussed above, depending on which other solid state form it is compared with, Form G of Plinabulin according to the present disclosure may have advantageous properties as described above. Plinabulin Form G shows stability upon heating and upon exposure to humidity.

The above form G can be prepared by a process comprising crystallizing Plinabulin Form G from a solution comprising Plinabulin and acetic acid.

Typically, the crystallization comprises dissolving Plinabulin in acetic acid and precipitating the said crystalline form to obtain a suspension.

Preferably, heating is used to dissolve Plinabulin. More preferably, the heating is to about to 80±5° C.

Typically, acetic acid is used at the range of 8 to 12 vol, preferably at about 10 vol.

Preferably, precipitation is done by cooling the said solution to obtain a suspension comprising the said form G. Preferably, cooling is to 10-30° C., or 15-25° C., and preferably about 20° C. Preferably, after cooling the suspension is further stirred. Preferably, stirring is performed at 15-30° C., or 18-25, and preferably about 20° C. Preferably, stirring is performed for a period of 15 minutes to about 2 hours, or 15 minutes to about 1 hour, and preferably about 30 min.

The present disclosure further comprises a crystalline form of Plinabulin designated as Form H. The crystalline Form H of Plinabulin can be characterized by data selected from one or more of the following: an XRPD pattern having peaks at 7.2, 8.5, 8.9, 12.2 and 17.0 degrees two theta±0.2 degrees two theta; an XRPD pattern substantially as depicted in FIG. 12; or combinations of these data. Crystalline Form H of Plinabulin may be further characterized by data selected from one or more of the following: an XRPD pattern having peaks at 7.2, 8.5, 8.9, 12.2 and 17.0 degrees two theta±0.2 degrees two theta; and also having one, two, three, four or five additional peaks selected from 15.2, 21.8, 23.1, 23.7 and 25.1 degrees two theta±0.2 degrees two theta.

Crystalline Form H may alternatively be characterized by an XRPD pattern having peaks at 7.2, 8.5, 8.9, 12.2, 15.2, 17.0, 21.8, 23.1, 23.7 and 25.1 degrees two theta.

Crystalline Form H of Plinabulin may be characterized by each of the above characteristics alone/or by all possible combinations, e.g. by XRPD pattern having peaks at 7.2, 8.5, 8.9, 12.2 and 17.0 degrees two theta±0.2 degrees two theta and an XRPD pattern as depicted in FIG. 12.

In some embodiments, crystalline Form H of Plinabulin may be optionally characterized as a DMSO solvate, preferably a disolvate of DMSO. Crystalline Form H of Plinabulin may contain about 29% to about 34% of DMSO. Preferably, crystalline Form H may be characterized by TGA thermogram showing weight loss of about 30.9% w/w as measured in the temperature range of 25-225° C. Preferably, crystalline Form H of Plinabulin may contain about 32% DMSO.

The present disclosure further comprises a crystalline form of Plinabulin designated as Form J. The crystalline Form J of Plinabulin can be characterized by data selected from one or more of the following: an XRPD pattern having peaks at 4.8, 9.0, 11.9, 13.4 and 14.4 degrees two theta±0.2 degrees two theta; an XRPD pattern substantially as depicted in FIG. 13; or combinations of these data. Crystalline Form J of Plinabulin may be further characterized by data selected from one or more of the following: an XRPD pattern having peaks at 4.8, 9.0, 11.9, 13.4 and 14.4 degrees two theta±0.2 degrees two theta; and also having one, two, three, four or five additional peaks selected from 17.4, 17.8, 19.2, 20.3 and 24.8 degrees two theta±0.2 degrees two theta.

Crystalline Form J may alternatively be characterized by an XRPD pattern having peaks at 4.8, 9.0, 11.9, 13.4, 14.4, 17.4, 17.8, 19.2, 20.3 and 24.8 degrees two theta±0.2 degrees two theta.

Crystalline Form J of Plinabulin may be characterized by each of the above characteristics alone/or by all possible combinations, e.g. by XRPD pattern having peaks at 4.8, 9.0, 11.9, 13.4 and 14.4 degrees two theta±0.2 degrees two theta and an XRPD pattern as depicted in FIG. 13.

In some embodiments, crystalline Form J of Plinabulin may be optionally characterized as a DMSO solvate. Crystalline Form J of Plinabulin may contain about 29% to 34% DMSO. Preferably, crystalline Form J of Plinabulin may be characterized by TGA thermogram showing weight loss of about 30.7% w/w as measured in the temperature range of 25-225° C. Preferably, may contain about 32% DMSO.

The present disclosure further comprises a crystalline form of Plinabulin designated as Form K. The crystalline Form K of Plinabulin can be characterized by data selected from one or more of the following: an XRPD pattern having peaks at 6.2, 12.4, 13.3, 21.6 and 24.5 degrees two theta±0.2 degrees two theta; an XRPD pattern substantially as depicted in FIG. 14; or combinations of these data. Crystalline Form K of Plinabulin may be further characterized by data selected from one or more of the following: an XRPD pattern having peaks at 6.2, 12.4, 13.3, 21.6 and 24.5 degrees two theta±0.2 degrees two theta; and also having one, two, three, four or five additional peaks selected from 17.6, 18.1, 19.5, 20.4 and 25.6 degrees two theta±0.2 degrees two theta.

Crystalline Form K may alternatively be characterized by an XRPD pattern having peaks at 6.2, 12.4, 13.3, 17.6, 18.1, 19.5, 20.4, 21.6, 24.5 and 25.6 degrees two theta±0.2 degrees two theta.

Crystalline Form K of Plinabulin may be characterized by each of the above characteristics alone/or by all possible combinations, e.g. by XRPD pattern having peaks at 6.2, 12.4, 13.3, 21.6 and 24.5 degrees two theta±0.2 degrees two theta and an XRPD pattern as depicted in FIG. 14.

In some embodiments, crystalline Form K of Plinabulin may be optionally characterized as a piperidine solvate. Crystalline Form K of Plinabulin may contain about 18% to about 22% DMSO. Preferably, may be characterized by TGA thermogram, showing weight loss step of 20.2% w/w as measured in the temperature range of 90–140° C. Preferably, may contain about 20% DMSO.

The present disclosure comprises an Amorphous form of Plinabulin. The Amorphous of Plinabulin can be characterized by data selected from one or more of the following: an XRPD pattern which does not show any sharp peaks by XRD pattern when measured at the range of 5-30 degrees two theta; an XRPD pattern substantially as depicted in FIG. 15; or combinations of these data. Origin of the small peak obtained at about 32.6 degrees two theta in FIG. 15 might be related to unknown inorganic impurity.

The present disclosure further comprises a crystalline form of Plinabulin designated as Plinabulin Form T. Plinabulin Form T can be characterized by data selected from one or more of the following: an XRPD pattern having peaks at 8.2, 9.5, 16.4, 21.5 and 24.7 degrees two theta±0.2 degrees two theta; an XRPD pattern substantially as depicted in FIG. 16; or combinations of these data. Crystalline Plinabulin Form T may be further characterized by data selected from one or more of the following: an XRPD pattern having peaks at 8.2, 9.5, 16.4, 21.5 and 24.7 degrees two theta±0.2 degrees two theta; and also having one, two, three, four or five additional peaks selected from 12.1, 14.0, 15.0, 18.4 and 22.5 degrees two theta±0.2 degrees two theta.

Crystalline Form T may alternatively be characterized by an XRPD pattern having peaks at 8.2, 9.5, 12.1, 14.0, 15.0, 16.4, 18.4, 21.5, 22.5 and 24.7 degrees two theta±0.2 degrees two theta.

Crystalline Plinabulin Form T may be characterized by each of the above characteristics alone/or by all possible combinations, e.g. by XRPD pattern having peaks at 8.2, 9.5, 16.4, 21.5 and 24.7 degrees two theta±0.2 degrees two theta and an XRPD pattern as depicted in FIG. 16.

In another embodiment, Crystalline Plinabulin Form T may optionally be characterized as a hydrate, preferably as monohydrate. Plinabulin Form T may contain from about 4% to about 6% of water, preferably about 5% of water, for example as measured by Karl Fischer instrument or by TGA (in Plinabulin, the theoretical stoichiometric amount of one water molecule is equal to 5.1%).

In one embodiment of the present disclosure, Plinabulin Form T is isolated.

In another embodiment of the present disclosure, Plinabulin Form T is polymorphically pure.

The present disclosure further comprises process for preparation of Plinabulin Form T comprising exposing amorphous Plinabulin to humidity.

Preferably, amorphous Plinabulin is exposed to 80-100% RH, more preferably to about 100% RH.

Preferably, amorphous Plinabulin is exposed to humidity for 12-48 hours, more preferably, for about 24 hours.

More preferably, amorphous Plinabulin is exposed to about 100% RH for about 24 hours.

The present disclosure comprises a crystalline form of Plinabulin designated as Form U. The crystalline Form U of Plinabulin can be characterized by data selected from one or more of the following: an XRPD pattern having peaks at 4.5, 7.8, 13.5, 16.3 and 18.1 degrees two theta±0.2 degrees two theta; an XRPD pattern substantially as depicted in FIG. 31; or combinations of these data. Crystalline Form U of Plinabulin may be further characterized by data selected from one or more of the following: an XRPD pattern having peaks at 4.5, 7.8, 13.5, 16.3 and 18.1 degrees two theta±0.2 degrees two theta; and also having one or two additional peaks selected from 10.1 and 20.5 degrees two theta±0.2 degrees two theta.

Crystalline Form U may alternatively be characterized by an XRPD pattern having peaks at 4.5, 7.8, 10.1, 13.5, 16.3, 18.1 and 20.5 degrees two theta±0.2 degrees two theta.

Crystalline Plinabulin Form U may be characterized by each of the above characteristics alone/or by all possible combinations, e.g. by XRPD pattern having peaks at 4.5, 7.8, 13.5, 16.3 and 18.1 degrees two theta±0.2 degrees two theta and an XRPD pattern as depicted in FIG. 31.

In another embodiment Crystalline Plinabulin Form U may optionally be characterized as an anhydrous form.

In one embodiment of the present disclosure, Plinabulin Form U is isolated.

In another embodiment of the present disclosure, Plinabulin Form U is polymorphically pure.

The above Form U can be prepared by a process comprising crystallizing Plinabulin Form U from chloroform, Typically, the crystallization comprises dissolving Plinabulin in chloroform and precipitating the said crystalline form to obtain a suspension.

Preferably, prior to dissolving Plinabulin in chloroform, a mixture comprising Plinabulin and chloroform is evaporated until dryness. Then, the concentrated mixture is combined with chloroform, and the combination is heated to obtain the said solution. Preferably, heating is to about reflux temperature.

Preferably, precipitation is done by cooling the said solution to obtain a suspension comprising the said form U, preferably, cooling is to −5° C. to about 10° C., or −5° C. to about 5° C., and preferably about 0° C.

The process for preparing crystalline form U may further comprise recovering the said crystalline form. The recovery may be done, for example, by filtering the suspension, washing and optionally by drying. Preferably, washing is done with chloroform. Preferably, drying is done by air. Preferably, drying is performed at room temperature.

Typically, 70-90 vol of chloroform, preferably about 80 vol of chloroform is used for preparing Plinabulin solutions.

Preferably, Plinabulin solution is heated to reflux temperature of about 55-62° C. more preferably to about 61° C.

Preferably, Plinabulin solution is heated for 15 minutes to about 1.5 hours, more preferably for about 30 min.

Optionally, filtration is used to obtain a clear solution of Plinabulin in chloroform.

The present disclosure comprises Plinabulin salts, such as hydrochloride salt.

The present disclosure further comprises a crystalline form of Plinabulin hydrochloride salt designated as Form Alpha. The crystalline Form Alpha of Plinabulin hydrochloride salt can be characterized by data selected from one or more of the following: an XRPD pattern having peaks at 9.2, 12.2, 13.6, 21.0 and 21.5 degrees two theta±0.2 degrees two theta; an XRPD pattern substantially as depicted in FIG. 8; a solid-state $^{13}$C NMR spectrum with signals at 158.2, 137.1, 122.4, 119.6 and 117.2±0.2 ppm; a solid state $^{13}$C NMR spectrum having the following chemical shift absolute differences from a peak at 109.1 ppm±1 ppm of 49.2, 28.0, 13.3, 10.5 and 8.1 ppm±0.1 ppm; a solid-state $^{13}$C NMR spectrum with signals at 158.2, 137.1, 132.5, 131.1, 129.4, 127.8, 127.0, 122.4, 119.6, 117.2, 109.1, 32.8 and 29.6 ppm±0.2 ppm; a solid-state $^{13}$C NMR spectrum as depicted in FIG. 24 or 25 or 26; or combinations of these data.

Crystalline Form Alpha of Plinabulin hydrochloride salt may alternatively be characterized by an XRPD pattern having peaks at 4.6, 9.2, 12.2, 13.6, 18.9, 19.7, 21.0, 21.5, 22.8 and 24.0 degrees two theta±0.2 degrees two theta.

Crystalline Form Alpha of Plinabulin hydrochloride salt may be characterized by each of the above characteristics alone/or by all possible combinations, e.g. by XRPD pattern having peaks at 9.2, 12.2, 13.6, 21.0 and 21.5 degrees two theta±0.2 degrees two theta and an XRPD pattern as depicted in FIG. 8.

Crystalline Form Alpha of Plinabulin hydrochloride salt may be further characterized by data selected from one or more of the following: an XRPD pattern having peaks at 9.2, 12.2, 13.6, 21.0 and 21.5 degrees two theta±0.2 degrees two theta; and also having one, two, three, four or five additional peaks selected from 4.6, 18.9, 19.7, 22.8 and 24.0 degrees two theta±0.2 degrees two theta; an FTIR spectrum having peaks at 1687, 1650, 1394, 1620, 1601, 1350, 761, 856, 691 and 1470 cm$^{-1}$±4 cm$^{-1}$; an FT-Raman spectrum having peaks at 1619, 1599, 1210, 526, 1649, 1001, 886, 1458, 1435 and 206 cm$^{-1}$±4 cm$^{-1}$ an FTIR spectrum as depicted in FIG. 27 or 28; Raman spectrum as depicted in FIG. 29 or 30; or combinations of these data.

In another embodiment crystalline Plinabulin hydrochloride Form Alpha may be optionally characterized as an anhydrous form, In one embodiment of the present disclosure, Plinabulin hydrochloride Form Alpha is isolated.

In another embodiment of the present disclosure, Plinabulin hydrochloride Form Alpha is polymorphically pure.

As discussed above, depending on which other solid state form it is compared with, Plinabulin hydrochloride Form Alpha, according to the present disclosure, may have advantageous properties. Particularly, the formation of hydrochloride salt enables the purification of Plinabulin for cases in which non-basic impurities present in the sample.

The above Plinabulin hydrochloride Form Alpha can be prepared by a process comprising suspending Plinabulin in mixture of DCM and methanol under heating and then adding hydrochloric acid.

The process for preparing Plinabulin hydrochloride Form Alpha may further comprise:
  a. providing a solution of Plinabulin in mixture of DCM and methanol
  b. adding hydrochloric acid to the solution
  c. cooling and filtering to get the wet product
  d. optionally, refluxing in THF, cooling and filtering Preferably, the ratio between DCM and methanol in stage a) is in the range of about 5:1 to about 0.5 particularly about 3:1 to about 1:1, and more preferably about 2:1.

Typically the solvent volume used in stage a) is at the range of 50 to 70 vol, preferably 55 to 65 vol, more preferably at the range of about 60 vol.

Preferably, the solution in stage a) is heated to about 45° C. for about 30 min.

Preferably, cooling the solution to 20 to 35° C., and preferably about 30° C. before adding the hydrochloric acid in stage b).

Optionally, in stage b) hydrochloric acid is added drop-wise.

Preferably, the suspension obtained in stage b) is stirred for 15 minutes to about 2 hours, or 15 minutes to 1 hour. Preferably the stirring is carried out at a temperature of 20 to 35° C. Preferably the stirring is carried out for about 30 min at about 30° C.

Preferably, recovery of the said crystalline form in stage c) may be done for example by cooling, stirring, by filtering the suspension, washing and optionally drying. Preferably, the cooling is to 15 to 25° C., preferably about 20° C. Preferably, the stirring is carried out for 10 to 24 hours, preferably for about 16 hours. Preferably, the washing is done with methanol.

Optionally, the wet product obtained in stage c) is suspended in THF at about reflux temperature.

The above Plinabulin hydrochloride Form Alpha can be prepared by a process comprising suspending Plinabulin in THF under heating and then adding hydrochloric acid.

The present disclosure further comprises process for preparation of Plinabulin hydrochloride form Alpha comprising:
  a. providing a solution of Plinabulin in THF
  b. adding hydrochloric acid to the solution
  c. cooling and optionally filtering to get wet product Typically, the THF volume used in stage a) is at the range of 54 to 64 vol, preferably at about 59 vol.

Preferably, Plinabulin is heated in stage a) to temperature range 30-40° C., more preferably to about 35° C.

Optionally in stage b) the hydrochloric acid is added drop-wise.

The suspension obtained in stage b) can be stirred while being heated. Preferably, the stirring is for 15 minutes to about 2 hours, or 15 minutes to about 1 hour, and preferably for about 30 min.

The process for preparing the above Form Alpha may further comprise recovery of the said crystalline form. The recovery may be done, for example, by cooling, stirring, filtering and washing. Preferably, the cooling is to a temperature of 10-25° C., or 15-22° C., and preferably about 20° C. Preferably, the stirring is for 0.5-3 hours, or 0.5-2 hours and preferably about 1 hour. Preferably the washing is carried out with THF.

The present disclosure further encompasses processes for preparing Plinabulin or solid state forms thereof. The process for preparing Plinabulin or solid state forms thereof comprises preparing the Plinabulin hydrochloride solid state form, according to the present disclosure, and converting it to Plinabulin or solid state forms thereof. The conversion can be done, for example, by reacting the solid state form of Plinabulin hydrochloride described herein with a suitable base to obtain Plinabulin.

The present disclosure also relates to the uses of any one or a combination of the solid state forms of Plinabulin, Plinabulin salts, including hydrochloride and solid state form thereof of the present disclosure, for preparing other solid state forms of Plinabulin and Plinabulin salts, such as hydrochloride salt of Plinabulin and solid state thereof.

The present disclosure also relates to any one or a combination of the above described solid state forms of Plinabulin and Plinabulin salts, including hydrochloride of the present disclosure, for use in preparing other solid state forms of Plinabulin and Plinabulin salts, such as hydrochloride salt, and solid state forms thereof.

In another aspect, the present disclosure encompasses the above described solid state forms of Plinabulin, Plinabulin salts, including hydrochloride, and solid state form thereof for use in the preparation of pharmaceutical compositions and/or formulations for use in medicine, preferably for treating cancer, such as breast, sarcoma, colon and prostate cancers.

The present disclosure also encompasses the uses of the above described solid state forms of Plinabulin and solid state forms of Plinabulin salts, including hydrochloride, for the preparation of pharmaceutical compositions and/or formulations, preferably for use in medicine, preferably for treating cancer, such as breast, sarcoma, colon and prostate cancers.

In yet another embodiment, the present disclosure encompasses pharmaceutical compositions comprising any one or a mixture of the solid state forms of Plinabulin and Plinabulin salts, including hydrochloride.

In yet another embodiment, the present disclosure encompasses pharmaceutical formulations comprising solid state forms of Plinabulin and solid state forms of Plinabulin salts, such as hydrochloride, when the pharmaceutical formulation comprising the solid state forms of Plinabulin and/or salts of Plinabulin, and at least one pharmaceutically acceptable excipient.

Pharmaceutical formulations of the present invention contain any one or a combination of the solid state forms of Plinabulin and salt thereof of the present invention, particularly crystalline Plinabulin Form G, Plinabulin Form U, Plinabulin Form T and Plinabulin hydrochloride Form Alpha. In addition to the active ingredient, the pharmaceutical formulations of the present invention can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present invention include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Plinabulin and Plinabulin hydrochloride and any other solid excipients are dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present invention, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present invention include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present invention is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present invention can be a capsule containing the composition, preferably a powdered or granulated solid composition of the invention, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, but they are not subjected to a final tableting step.

A pharmaceutical formulation of Plinabulin can be administered. Plinabulin is preferably formulated for administration to a mammal, preferably a human, by injection. Plinabulin can be formulated, for example, as a viscous liquid solution or suspension, preferably a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

Having described the disclosure with reference to certain preferred embodiments, other embodiments will become apparent to one skilled in the art from consideration of the specification. The disclosure is further illustrated by reference to the following examples describing in detail the preparation of the composition and methods of use of the disclosure. It will be apparent to those skilled in the art that many modifications, both to materials and methods, may be practiced without departing from the scope of the disclosure.

Analytical Methods

Powder X-ray Diffraction was performed on an X-Ray powder diffractometer PanAlytical X'pert Pro; CuKα radiation ($\lambda$=1.541874 Å); X'Celerator detector with active length 2.122 degrees 2-theta; laboratory temperature 25±3° C.; zero background sample holders. Prior to analysis, the samples were gently ground using a mortar and pestle to obtain a fine powder. The ground sample was adjusted into a cavity of the sample holder and the surface of the sample was smoothed using a cover glass. The parameters for X-ray Powder diffraction pattern ("XRPD") method:

| | |
|---|---|
| Scan range | 3-40 degrees 2-theta |
| Scan mode | continuous |
| Step size | 0.0167 degrees |
| Step size | 42 s |
| Sample spin | 60 rpm |
| Sample holder | zero background silicon plate |

Thermogravimetric Analysis (TGA) Method

TGA measurements were performed on a Thermogravimetric analyzer TGA Discovery (TA Instruments). Aluminum crucibles 100 μl were used for sample preparation. Usual sample weight was between 5 and 15 mg.

Measurement Parameters:

| | |
|---|---|
| Temperature range at least | 25-300° C.; |
| Heating rate | 10° C./min; |
| Nitrogen flow | 25 ml/min. |

FTIR Spectroscopy Method

KBr pellet was prepared and FTIR transmission spectrum was recorded on Nicolet 380 spectrometer, equipped with KBr beam splitter and DTGS KBr detector.

Instrument Parameters:

| | |
|---|---|
| Spectral range: | 4000-400 cm$^{-1}$ |
| Resolution: | 4.0 cm$^{-1}$ |
| Number of scans: | 64 |
| Sample gain: | 1 |
| Optical velocity: | 0.6329 |
| Aperture: | 100 |

FT-Raman Spectroscopy Method

Powder samples were filled into 5 mm NMR tube and Raman spectrum was recorded on Nicolet 6700 FT-IR spectrometer with NXR FT-Raman module, equipped with 1064 nm Nd:YVO4 excitation laser, CaF$_2$ beam splitter and Ge detector.

Instrument Parameters:

| | |
|---|---|
| Spectral range: | 3700-150 cm$^{-1}$ |
| Resolution: | 4.0 cm$^{-1}$ |
| Number of scans: | 64 |
| Sample gain: | auto |
| Optical velocity: | 0.4747 |
| Aperture: | 59.79 |
| Laser power: | 0.2 W-1 W |

$^{13}$C Solid State NMR Method $^{13}$C CP/MAS NMR spectra were measured at 125 MHz using Bruker Avance III 500 WB/US NMR spectrometer (Karlsruhe, Germany, 2003) at magic angle spinning (MAS) frequency $\omega_r/2\pi=11$ kHz. In all cases finely powdered samples were placed into 4-mm ZrO$_2$ rotors and the standard "cpmas" pulseprogram was used. During acquisition of the data the high-power dipolar decoupling "TPPM" (two-pulse phase-modulated) was applied. The flip-pulse length was 4.8 μs. Applied nutation frequency of B$_1$($^1$H) field was $\omega_1/2\pi=89.3$ kHz. Nutation frequency of B$_1$($^{13}$C) and B$_1$($^1$H) fields during cross-polarization was $\omega_1/2\pi=62.5$ kHz. The number of scans was 2048. Taking into account frictional heating of the samples during fast rotation all NMR experiments were performed at 293 K (precise temperature calibration was performed).

The NMR spectrometer was completely calibrated and all experimental parameters were carefully optimized prior the investigation of samples. Magic angle was set using KBr during standard optimization procedure and homogeneity of magnetic field was optimized using adamantane sample (resulting line-width at half-height $\Delta v_{1/2}$ was less than 3.5 Hz at 250 ms of acquisition time).

EXAMPLES

Plinabulin can be obtained by any procedure described in the literature, for example using the syntheses procedure reported in WO2004054498.

Plinabulin forms 1, 5 and 6 which were used in some examples below can be prepared according to procedures described in PCT application WO2017011399.

Example 1. Preparation of Plinabulin Form A

Plinabulin (500 mg) were dissolved at 80° C. in DMF (dimethylformamide, 10.5 ml). The obtained solution was concentrated under reduced pressure (rotary evaporator) at 70-80° C. to get a yellow solid (Form A by XRD analysis). The solid residue was dissolved in a mixture of EtOAc (Ethylacetate, 100 ml) and DMF (dimethylformamide, 2 ml) and washed with water (10 ml) in a separatory funnel. The phases were separated and the organic phase was concentrated under reduced pressure (rotary evaporator) affording a yellow solid (Form A by XRPD, FIG. 1).

Example 2. Preparation of Plinabulin Form B

A solution of Plinabulin (500 mg) in trifluoroethanol (6 ml) was stirred at 75° C. for 30 minutes. The mixture was cooled to 20° C. in one hour and then to 0° C. in another hour. After stirring at 0° C. for additional 30 minutes, the compound was filtered to afford Plinabulin as a yellow solid (420 mg, Form B by XRD, FIG. 2).

Example 3. Preparation of Plinabulin Form C

Plinabulin Form B (300 mg) was dried for 16 hours at 50° C. in a vacuum oven under reduced pressure (about 50-500 mbr) afford Plinabulin Form C by XRPD (230 mg, FIG. 3).

Example 4. Preparation of Plinabulin Form D

Plinabulin (100 mg, Form 5) was placed in a saturated atmosphere of pyridine for 20 days at RT to afford Form D (FIG. 4).

Example 5. Preparation of Plinabulin Form E

A suspension of Plinabulin (44 mg) in morpholine (1 ml) was heated to 124° C. in 30 minutes to afford a clear solution. The solution was then stirred at 124° C. for 15 minutes, cooled to −5° C. in 1 hour and then left at −5° C. for 30 minutes. The obtained suspension was finally centrifuged and the upper solution was removed to afford Plinabulin as a yellow solid (30 mg, Form E by XRPD, FIG. 5).

Example 6. Preparation of Plinabulin Form F

A suspension of Plinabulin (45 mg, mainly form 1) in N-methyl-morpholine (0.5 ml) was heated to 110° C. in 30 minutes, stirred at 110° C. for 30 minutes, cooled to 0° C. in 2 hour and then kept at 0° C. for 1 hour. The suspension was finally centrifuged and the upper solution was removed to afford Plinabulin precipitation as a yellow solid (40 mg, Form F by XRPD, FIG. 6).

Example 7. Preparation of Plinabulin Form G

Plinabulin (330 mg, Form 5) was dissolved in acetic acid (3.4 ml) at 80° C. After stirring the solution at 80° C. for 30 minutes, the reaction mixture was cooled to 20° C. in one hour and then stirred at 20° C. for 30 minutes. The compound was filtered to afford Plinabulin as a yellow solid (169 mg, Form G by XRPD, FIG. 7).

Example 8. Preparation of Plinabulin Hydrochloride Form Alpha (Process A)

Plinabulin (5 g, Form 6) was suspended in DCM (dichloromethane)/MeOH 2:1 solution (200 ml). The opalescent solution was warmed and stirred for 30 min at 45° C. After cooling to 30° C. in 10 minutes, 6 N HCl (10 ml) was added drop-wise in 5 minutes. The obtained suspension was stirred at 30° C. for 30 minutes and then cooled to 20° C. and left under stirring for 16 hours. The solid was then filtered and washed with MeOH (10 ml). The wet solid (6.5 g) was suspended in THF (tetrahydrofuran) (30 ml) and refluxed for 30 minutes. The reaction mixture was cooled to 20° C. in 1 hour and was filtered after 1 additional hour. The obtained solid was washed with THF (10 ml). Plinabulin Hydrochloride was obtained as an off-white powder (3.5 g, Form Alpha, FIG. 8).

Example 9. Preparation of Plinabulin Hydrochloride Form Alpha (Process B)

To an opalescent solution of Plinabulin (5 g, Form 6) in THF (300 ml) at 35° C., 6N HCl (6 g) was added drop-wise in 5 minutes. The obtained suspension was stirred at 30° C. for 30 minutes and then cooled to 20° C. and stirred at this temperature for 1 hour. The solid was then filtered and washed with THF (10 ml). Plinabulin Hydrochloride was obtained as an off-white powder (Form Alpha, confirmed by XRPD).

Example 10. Preparation of Plinabulin Form H

Plinabulin (97 mg) was dissolved in DMSO (dimethyl sulfoxide, 2.5 ml). The obtained solution was filtered on a 0.5 µm membrane and the filtrate solution was immediately cooled to −70° C. by placing it in dry ice/acetone bath. The cooled filtrate was placed in the lyophilizer pre-cooled at −40° C. The temperature during lyophilization was maintained at 10° C. The final compound was obtained as a yellow powder (Form H, FIG. 12).

Example 11. Preparation of Plinabulin Form J

Plinabulin (250 mg) was dissolved in DMSO (2 ml) and tert-butanol (6 ml). The obtained solution was filtered on a 0.5 µm membrane and the filtrate solution was immediately cooled to −70° C. by placing it in dry ice/acetone bath. The cooled filtrate was placed in the lyophilizer pre-cooled at −40° C. The temperature during lyophilization was maintained at 10° C. The final compound was obtained as a yellow powder (Form J, FIG. 13).

Example 12. Preparation of Plinabulin Form K

Plinabulin (100 mg) was suspended in piperidine (0.5 ml) and the mixture was heated till a clear solution was obtained. The solution was allowed to reach the room temperature and the obtained suspension was filtered to afford Plinabulin as a yellow solid (Form K, FIG. 14).

Example 13. Preparation of Amorphous Plinabulin

In a glass vial, Plinabulin (200 mg, Form 5) was suspended in water (2 ml). The mixture was immediately placed in a dry ice/acetone bath at −70° C. and then the sample was freeze-dried in a lyophilizer pre-cooled at −40° C. The temperature during lyophilization was maintained below 10° C. The final compound was obtained as a yellow powder which was analyzed by XRD, to show amorphous content as shown in FIG. 15.

Example 14. Preparation of Plinabulin Form T

Plinabulin (100 mg, amorphous, prepared by Example 1) was placed for 24 hrs under humidity conditions having 100% RH at RT. The obtained material (100 mg) was analyzed by XRD. According to XRD pattern, Plinabulin Form T was obtained (as shown by FIG. 16.

Example 15. Preparation of Plinabulin Form U

A mixture of Plinabulin (4.2 g) in chloroform (350 ml) was warmed to reflux and the obtained slightly cloudy mixture was clarified by filtration on a dicalite pad. The clear solution was then concentrated under vacuum at atmospheric pressure till evaporation completed. Chloroform (42 ml) was added under stirring and the obtained suspension was refluxed for 30 minutes (about 61° C.). The mixture was then cooled to 0° C. in 30 minutes and left at this temperature for an additional hour. The obtained yellow solid was filtered to afford about 3.7 g of Plinabulin Form U, as confirmed by XRD (FIG. 31).

The invention claimed is:

1. A crystalline form of Plinabulin designated as Form G, characterized by
    an X-ray powder diffraction pattern having peaks at 8.0, 10.6, 17.9, 18.2 and 24.8 degrees 2-theta±0.2 degrees 2-theta, and also having one, two or three additional peaks selected from 5.9, 11.4, and 15.2 degrees two theta±0.2 degrees two theta; or
    an XRPD pattern as depicted in FIG. 7.
2. The crystalline Form G of Plinabulin according to claim 1, characterized by
    an XRPD pattern having peaks at 8.0, 10.6, 17.9, 18.2 and 24.8 degrees 2-theta±0.2 degrees 2-theta, and also having one, two or three additional peaks selected from 5.9, 11.4, and 15.2 degrees two theta±0.2 degrees two theta, and also one or more of the following:
    a. an FTIR spectrum having peaks at 1670, 1659, 1631, 1452, 1416, 1371, 1350, 1318, 1258 and 955 cm$^{-1}$±4 cm$^{-1}$;
    b. an FTIR spectrum substantially as depicted in FIG. 20 or 21;
    c. an FT-Raman spectrum having peaks at 1673, 1600, 1453, 1417, 1320, 1273, 1207, 1189, 1000 and 513 cm$^{-1}$±4 cm$^{-1}$; or
    d. an FT-Raman spectrum substantially as depicted in FIG. 22 or 23.
3. A pharmaceutical composition comprising a crystalline form according to claim 1.
4. A pharmaceutical formulation comprising a crystalline form according to claim 1, and at least one pharmaceutically acceptable excipient.
5. The crystalline form according to claim 1, for use as a medicament.
6. The crystalline form, according to claim 1, for use in the treatment of cancer.
7. The crystalline form, according to claim 1, for the manufacture of medicament for treating cancer.

8. The crystalline of Plinabulin according to claim 1, further comprising:
   a. a solid state $^{13}$C-NMR spectrum having characteristic peaks at 174.7, 160.0, 140.7, 131.4 and 124.1 ppm±0.2 ppm;
   b. a solid state $^{13}$C-NMR spectrum having the following chemical shift absolute differences from a reference peak at 105.9 ppm±1 ppm of 68.8, 54.1, 34.8, 25.5 and 18.1 ppm±0.1 ppm;
   c. a solid state $^{13}$C-NMR spectrum having characteristic peaks at 174.7, 160.0, 154.5, 140.7, 131.4, 128.0, 124.1, 116.3, 115.0, 107.4, 105.9, 31.3 and 18.2 ppm±0.2 ppm;
   d. a solid state $^{13}$C-NMR spectrum as depicted in FIG. 17 or 18 or 19; or
   e. a combination of any two or more of the above.

9. A process for preparing a pharmaceutical formulation, comprising combining a crystalline form according to claim 1, with at least one pharmaceutically acceptable excipient.

10. A method of treating cancer, comprising administering a therapeutically effective amount of a crystalline form according to claim 1, to a subject suffering from cancer.

11. A crystalline form of Plinabulin designated as Form G, characterized by an X-ray powder diffraction pattern having peaks at 5.9, 8.0, 10.6, 11.4, 12.2, 13.1, 15.2, 17.9, 18.2 and 24.8 degrees 2-theta±0.2 degrees 2-theta.

12. The crystalline Form G of Plinabulin according to claim 11, wherein the crystalline Form G of Plinabulin is an acetic acid solvate.

\* \* \* \* \*